US010449077B2

(12) United States Patent
Grim et al.

(10) Patent No.: US 10,449,077 B2
(45) **Date of Patent: *Oct. 22, 2019**

(54) ADJUSTABLE WALKING APPARATUS

(71) Applicant: Ortho Systems, Agoura Hills, CA (US)

(72) Inventors: Tracy E. Grim, Thousand Oaks, CA (US); Steve Eastwood, Los Angeles, CA (US); Kenji Watabe, Ventura, CA (US); Mark Scott Nelson, Sr., Simi Valley, CA (US); Dwight Paul Bennett, Seattle, WA (US); Steven L. Hecker, Los Angeles, CA (US)

(73) Assignee: Ovation Medical, Agoura Hills, CA (US)

(*) Notice: Subject to any disclaimer, the term of this patent is extended or adjusted under 35 U.S.C. 154(b) by 259 days.

This patent is subject to a terminal disclaimer.

(21) Appl. No.: 15/336,650

(22) Filed: Oct. 27, 2016

(65) Prior Publication Data

US 2017/0135838 A1 May 18, 2017

Related U.S. Application Data

(63) Continuation of application No. 14/789,918, filed on Jul. 1, 2015, now Pat. No. 9,510,965.

(Continued)

(51) Int. Cl.
*A61F 5/01* (2006.01)
*A43B 7/20* (2006.01)

(52) U.S. Cl.
CPC .............. *A61F 5/0111* (2013.01); *A43B 7/20* (2013.01)

(58) Field of Classification Search
CPC ........ A61F 5/0111; A61F 5/01; A61F 5/0193; A61F 5/0102; A61F 5/0116; A61F 5/012;

(Continued)

(56) References Cited

U.S. PATENT DOCUMENTS 143,537 A 10/1873 Silberschmidt
1,472,415 A 10/1923 Haggerty (Continued)

FOREIGN PATENT DOCUMENTS

CN 201085714 Y 7/2008
CN 101766361 A * 7/2010

(Continued)

OTHER PUBLICATIONS

PCT Publication No. WO/87/03471, dated Jun. 18, 1987, regarding PCT Application No. PCT/US86/02670.

(Continued)

*Primary Examiner* — Ophelia A Hawthorne
(74) *Attorney, Agent, or Firm* — Fulwider Patton LLP; Michael J. Moffatt, Esq.

(57) ABSTRACT

A walking apparatus is provided that includes a sole having an adjustable length, the sole comprising a heel portion, a forefoot portion operatively coupled to the heel portion, the forefoot portion configured for adjustment from a first position to at least one other position relative to the heel portion, wherein a length of the sole is configured to adjust from a first length to a second length when the forefoot portion is adjusted from the first position to the at least one other position.

18 Claims, 36 Drawing Sheets

1000
1016c
1016d
1016b
1008
1020
1016a
1018
1012
1014
1010
1006
1002
1004

Related U.S. Application Data

(60) Provisional application No. 62/019,839, filed on Jul. 1, 2014.

(58) Field of Classification Search
CPC ...... A61F 5/0123; A61F 5/019; A61F 5/0127; A61F 13/066; A61F 5/0104; A61F 5/0125; A61F 5/0113; A61F 2250/001; A61F 5/0585; A61F 2005/0158; A61F 2005/0167; A61F 5/14; A61F 13/043; A61F 13/064; A43B 7/20; A43B 3/26
See application file for complete search history.

(56) References Cited

U.S. PATENT DOCUMENTS 2,565,707 A 8/1951 Walsh
2,643,468 A 6/1953 Gottschalk
2,772,196 A 11/1956 Pooley
2,959,169 A 11/1960 Bless
3,296,490 A 1/1967 Price
3,464,126 A 9/1969 Sarkissian
3,504,668 A 4/1970 Boudon
3,661,151 A 5/1972 Schoenbrun et al.
3,665,619 A 5/1972 Gray
3,792,537 A 2/1974 Plank et al.
3,805,773 A 4/1974 Sichau
3,814,088 A 6/1974 Raymond
3,955,565 A 5/1976 Johnson, Jr.
3,976,059 A 8/1976 Lonardo
4,005,704 A 2/1977 Stöhr et al.
4,053,995 A 10/1977 Shein
4,057,056 A 11/1977 Payton
4,094,312 A 6/1978 Whyte
4,100,686 A 7/1978 Sgarlato et al.
4,100,918 A 7/1978 Glancy
4,184,273 A 1/1980 Boyer et al.
4,188,735 A 2/1980 Hahn
4,215,491 A 8/1980 Giannetti
4,217,706 A 8/1980 Vartanian
4,265,033 A 5/1981 Pois
4,268,931 A 5/1981 Salomon
4,393,866 A 7/1983 Finnieston
4,446,856 A 5/1984 Jordan
4,454,871 A 6/1984 Mann et al.
4,494,536 A 1/1985 Latenser
4,497,070 A 2/1985 Cho
4,505,269 A 3/1985 Davies et al.
4,510,927 A 4/1985 Peters
4,550,721 A 11/1985 Michel
4,556,054 A 12/1985 Paulseth
4,559,934 A 12/1985 Philipp
4,567,678 A 2/1986 Morgan et al.
4,572,169 A 2/1986 Mauldin et al.
4,587,962 A 5/1986 Greene et al.
4,590,932 A 5/1986 Wilkerson
4,624,247 A 11/1986 Ford
4,628,945 A 12/1986 Johnson, Jr.
4,665,904 A 5/1987 Lerman
4,771,768 A 9/1988 Crispin
4,805,601 A 2/1989 Eischen, Sr.
4,825,856 A 5/1989 Nelson
4,844,094 A 7/1989 Grim
4,862,900 A 9/1989 Hefele
4,872,273 A 10/1989 Smeed
4,879,822 A 11/1989 Hayes
4,919,118 A 4/1990 Morris
4,941,271 A 7/1990 Lakic
4,947,838 A 8/1990 Giannetti
4,964,402 A 10/1990 Grim et al.
4,974,583 A 12/1990 Freitas
4,982,733 A 1/1991 Broadhurst et al.
4,989,349 A 2/1991 Ellis, III
4,999,932 A 3/1991 Grim
5,020,523 A 6/1991 Bodine
5,078,128 A 1/1992 Grim et al.
5,086,761 A 2/1992 Ingram
5,088,478 A 2/1992 Grim
5,088,479 A 2/1992 Detoro
5,088,481 A 2/1992 Darby
5,092,321 A 3/1992 Spademan
5,125,400 A 6/1992 Johnson, Jr.
5,154,695 A 10/1992 Farris et al.
5,176,623 A 1/1993 Stetman et al.
5,197,942 A 3/1993 Brady
5,213,564 A 5/1993 Johnson, Jr. et al.
5,219,324 A 6/1993 Hall
5,226,245 A 7/1993 Lamont
5,226,875 A 7/1993 Johnson
5,233,767 A 8/1993 Kramer
5,242,379 A 9/1993 Harris et al.
5,277,695 A 1/1994 Johnson, Jr. et al.
RE34,661 E 7/1994 Grim
5,329,705 A 7/1994 Grim et al.
5,330,419 A 7/1994 Toronto
5,334,135 A 8/1994 Grim et al.
5,352,189 A 10/1994 Schumann et al.
5,353,525 A 10/1994 Grim
5,367,789 A 11/1994 Lamont
5,368,551 A 11/1994 Zuckerman
5,370,133 A 12/1994 Darby et al.
5,370,604 A 12/1994 Bernardoni
5,378,223 A 1/1995 Grim et al.
5,383,290 A 1/1995 Grim
5,384,970 A 1/1995 Melton
5,392,534 A 2/1995 Grim
5,399,152 A 3/1995 Habermeyer et al.
5,399,155 A 3/1995 Strassburg et al.
5,407,421 A 4/1995 Goldsmith
5,425,701 A 6/1995 Oster et al.
5,426,872 A 6/1995 Hayes
5,429,588 A 7/1995 Young et al.
5,441,015 A 8/1995 Farley
5,445,602 A 8/1995 Grim et al.
5,460,599 A 10/1995 Davis et al.
5,464,385 A 11/1995 Grim
5,483,757 A 1/1996 Frykberg
5,496,263 A 3/1996 Fuller, II et al.
5,503,622 A 4/1996 Wehr
5,507,720 A 4/1996 Lampropoulos
5,526,586 A 6/1996 Foscaro
5,527,269 A 6/1996 Reithofer
5,551,950 A 9/1996 Oppen
5,554,104 A 9/1996 Grim
5,571,077 A 11/1996 Klearman et al.
5,577,998 A 11/1996 Johnson, Jr. et al.
5,582,579 A 12/1996 Chism et al.
5,609,570 A 3/1997 Lamont
5,617,650 A 4/1997 Grim
5,620,411 A 4/1997 Schumann et al.
5,632,723 A 5/1997 Grim
5,641,322 A 6/1997 Silver et al.
5,675,839 A 10/1997 Gordon et al.
5,720,715 A 2/1998 Eriksson
5,761,834 A 6/1998 Grim et al.
5,762,622 A 6/1998 Lamont
5,772,619 A 6/1998 Corbett
5,776,090 A 7/1998 Bergmann et al.
5,799,659 A 9/1998 Stano
5,823,981 A 10/1998 Grim et al.
5,827,210 A 10/1998 Antar et al.
5,827,211 A 10/1998 Sellinger
5,833,639 A 11/1998 Nune et al.
5,836,902 A 11/1998 Gray
5,853,381 A 12/1998 Stevenson et al.
5,857,987 A 1/1999 Habermeyer
5,865,166 A 2/1999 Fitzpatrick et al.
5,868,690 A 2/1999 Eischen, Sr.
5,887,591 A 3/1999 Powell et al.
5,891,073 A 4/1999 Deirmendjian et al.
5,897,515 A 4/1999 Willner et al.
5,897,520 A 4/1999 Gerig
5,902,259 A 5/1999 Wilkerson
5,913,841 A 6/1999 Lamont
5,925,010 A 7/1999 Caprio, Jr.

(56) References Cited

U.S. PATENT DOCUMENTS 5,951,504 A 9/1999 Iglesias et al.
5,954,075 A 9/1999 Gilmour
5,961,477 A 10/1999 Turtzo
5,971,946 A 10/1999 Quinn et al.
5,980,475 A 11/1999 Gibbons
5,993,404 A 11/1999 Mc Niel
6,019,741 A 2/2000 Prieskorn
6,021,780 A 2/2000 Darby
6,024,712 A 2/2000 Iglesia et al.
6,027,468 A 2/2000 Pick
6,044,578 A 4/2000 Kelz
6,056,712 A 5/2000 Grim
6,115,945 A 9/2000 Ellis, III
6,126,625 A 10/2000 Lundberg
6,146,349 A 11/2000 Rothschild et al.
6,154,983 A 12/2000 Austin
6,155,998 A 12/2000 Gilmour
6,189,172 B1 2/2001 Baek
6,228,044 B1 5/2001 Jensen et al.
6,247,250 B1 6/2001 Hauser
6,267,742 B1 7/2001 Krivosha et al.
6,269,554 B1 8/2001 Silvestrini et al.
6,277,087 B1 8/2001 Hess et al.
6,282,816 B1 9/2001 Rosendahl
6,282,818 B1 9/2001 Lu
6,334,854 B1 1/2002 Davis
6,350,246 B1 2/2002 DeToro
6,361,514 B1 3/2002 Brown et al.
6,361,515 B1 3/2002 Gilmour
6,374,516 B1 4/2002 Bonaventure et al.
6,406,450 B1 6/2002 Kowalczyk et al.
6,409,695 B1 6/2002 Connelly
6,432,073 B2 8/2002 Prior et al.
6,491,654 B2 12/2002 Lamont
D473,654 S 4/2003 Iglesias et al.
6,558,339 B1 5/2003 Graham
6,572,571 B2 6/2003 Lowe
6,648,843 B1 11/2003 Marciano et al.
6,656,145 B1 12/2003 Morton
6,682,497 B2 1/2004 Jensen et al.
6,699,209 B2 3/2004 Turtzo
6,711,834 B1 3/2004 Kita
6,722,060 B2 4/2004 Okajima
6,755,798 B2 6/2004 McCarthy et al.
6,793,638 B1 9/2004 DeToro et al.
6,796,058 B2 9/2004 Potchatko
D500,855 S 1/2005 Pick et al.
6,866,043 B1 3/2005 Davis
6,923,780 B2 8/2005 Price et al.
6,945,946 B2 9/2005 Rooney
6,945,947 B2 9/2005 Ingimundarson et al.
6,955,654 B2 10/2005 Gilmour
6,976,972 B2 12/2005 Bradshaw
6,979,287 B2 12/2005 Elbaz et al.
6,991,613 B2 1/2006 Sensabaugh
7,018,351 B1 3/2006 Iglesias et al.
7,018,352 B2 3/2006 Pressman et al.
D519,211 S 4/2006 Doty et al.
7,077,818 B2 7/2006 Ingimundarson et al.
7,163,518 B1 1/2007 Roche et al.
7,163,519 B2 1/2007 Price et al.
7,182,743 B2 2/2007 Slautterback et al.
D541,085 S 4/2007 Marsilio
7,288,076 B2 10/2007 Grim et al.
7,291,181 B1 11/2007 Lyons et al.
7,294,114 B1 11/2007 Clement et al.
7,303,538 B2 12/2007 Grim et al.
7,311,686 B1 12/2007 Iglesias et al.
7,354,411 B2 4/2008 Perry et al.
7,384,584 B2 6/2008 Jerome et al.
7,418,755 B2 9/2008 Bledsoe et al.
7,475,501 B1 1/2009 DeToro et al.
7,563,238 B1 7/2009 Breashears
7,569,022 B2 8/2009 Morinaka
7,585,285 B2 9/2009 Pone et al.
7,597,674 B2 10/2009 Hu et al.
7,666,157 B2 2/2010 Win
D616,556 S 5/2010 Hu
7,727,173 B2 6/2010 Rooney
7,727,174 B2 6/2010 Chang et al.
7,743,532 B2 6/2010 Bledsoe et al.
D619,726 S 7/2010 Win
7,758,529 B2 7/2010 Jensen et al.
7,867,182 B2 1/2011 Iglesias et al.
D634,438 S 3/2011 Hu
7,896,826 B2 3/2011 Hu et al.
7,918,813 B2 4/2011 Drake et al.
7,922,677 B2 4/2011 Daiju
D640,792 S 6/2011 Anderson et al.
D641,084 S 7/2011 Anderson et al.
D642,695 S 8/2011 Anderson et al.
8,002,724 B2 8/2011 Hu et al.
D645,153 S 9/2011 Anderson et al.
8,012,112 B2 9/2011 Barberio
D662,598 S 6/2012 Anderson et al.
8,226,585 B2 7/2012 Pick et al.
8,251,932 B2 8/2012 Fout
8,251,936 B2 8/2012 Fout et al.
9,510,965 B2* 12/2016 Grim .................... A61F 5/0111
2001/0027616 A1 10/2001 Silvestrini et al.
2002/0062579 A1 5/2002 Caeran
2002/0073578 A1 6/2002 Ellis, III
2002/0128574 A1 9/2002 Darby
2003/0196352 A1 10/2003 Bledsoe et al.
2004/0015112 A1 1/2004 Salutterback et al.
2004/0030275 A1 2/2004 Morinaka
2005/0016020 A1 1/2005 Ellis, III
2005/0131324 A1 6/2005 Bledsoe
2005/0171461 A1 8/2005 Pick
2005/0172517 A1 8/2005 Bledsoe et al.
2005/0228332 A1 10/2005 Bushby
2005/0240133 A1 10/2005 Rooney
2005/0274046 A1 12/2005 Schwartz
2006/0032093 A1 2/2006 Vannini
2006/0048344 A1 3/2006 Cavanagh et al.
2006/0084899 A1 4/2006 Verkade et al.
2006/0189907 A1 8/2006 Pick et al.
2006/0217649 A1 9/2006 Rabe
2007/0010770 A1 1/2007 Gildersleeve
2007/0107267 A1 5/2007 Hodgson
2007/0191749 A1 8/2007 Barberio
2007/0260164 A1 11/2007 Chiodo et al.
2007/0276307 A1 11/2007 Erenstone
2007/0293798 A1 12/2007 Hu et al.
2008/0004558 A1 1/2008 Outred et al.
2008/0060220 A1 3/2008 Lyden
2008/0098626 A1 5/2008 Wright
2008/0154166 A1 6/2008 Beckwith et al.
2008/0294082 A1 11/2008 Chang et al.
2008/0294083 A1 11/2008 Chang et al.
2008/0302371 A1 12/2008 Cohen et al.
2008/0319362 A1 12/2008 Joseph
2009/0043234 A1 2/2009 Bledsoe et al.
2009/0076425 A1 3/2009 Schwartz
2009/0099495 A1 4/2009 Campos et al.
2009/0133292 A1 5/2009 Salvatelli et al.
2009/0192427 A1 7/2009 Brown et al.
2009/0192428 A1 7/2009 DeBoer et al.
2009/0199429 A1 8/2009 Ellis
2009/0227927 A1 9/2009 Frazer
2009/0227928 A1 9/2009 Drake et al.
2009/0264803 A1 10/2009 Darby, II et al.
2009/0287127 A1 11/2009 Hu et al.
2009/0299246 A1 12/2009 Pone et al.
2009/0306565 A1 12/2009 Chan
2010/0010410 A1 1/2010 Hu et al.
2010/0069807 A1 3/2010 Cox
2010/0100018 A1 4/2010 Fout
2010/0204631 A1 8/2010 Rooney
2010/0234782 A1 9/2010 Hu et al.
2011/0009791 A1 1/2011 Hopmann
2011/0015555 A1 1/2011 Anderson et al.
2011/0021963 A1 1/2011 Graddon et al.
2011/0066095 A1 3/2011 Price et al.

(56) References Cited

U.S. PATENT DOCUMENTS

| | | | |
|---|---|---|---|
| 2011/0146032 | A1 | 6/2011 | Hu et al. |
| 2011/0196275 | A1 | 8/2011 | Chang et al. |
| 2011/0196276 | A1 | 8/2011 | Kuhn |
| 2011/0313336 | A1 | 12/2011 | Chan |
| 2012/0000092 | A1 | 1/2012 | Ingvarsson et al. |
| 2012/0010534 | A1 | 1/2012 | Kubiak et al. |
| 2012/0010535 | A1 | 1/2012 | Kubiak et al. |
| 2012/0035520 | A1 | 2/2012 | Ingimundarson et al. |
| 2012/0078148 | A1 | 3/2012 | Hu et al. |
| 2012/0116275 | A1 | 5/2012 | Pochatko |
| 2012/0137544 | A1 | 6/2012 | Rosa et al. |
| 2013/0066247 | A1 | 3/2013 | Bird et al. |
| 2013/0226059 | A1 | 8/2013 | Morris |

FOREIGN PATENT DOCUMENTS

| | | |
|---|---|---|
| CN | 201523712 U | 7/2010 |
| DE | 2341658 | 3/1974 |
| DE | 3228753 | 2/1984 |
| DE | 3909922 | 2/1990 |
| EP | 0095396 | 11/1983 |
| EP | 1006960 | 1/2003 |
| FR | 2399811 | 3/1979 |
| RU | 2165229 | 4/2001 |

OTHER PUBLICATIONS

Article from http://www.alimed.com regarding AliMed D2 Night Splint for Plantar Fasciitis.

PCT Publication No. WO2012/020251, dated Feb. 16, 2012, regarding PCT Application No. PCT/GB2011/051499.

PCT Publication No. WO/2005/097014, dated Oct. 20, 2005, regarding PCT Application No. PCT/SE2005/000513.

PCT Publication No. WO/2012/099989, dated Jul. 26, 2013, regarding PCT Application No. PCT/US2012/021763.

PCT Publication No. WO/2012/001678, dated Jan. 5, 2012, regarding PCT Application No. PCT/IL2011/000487.

Paul A. Dale, M.D. et al.; “A New Concept in Fracture Immobilization”, Clinical Orthopaedics. Oct. 1993, vol. 295: 264-269.

Aircast Incorporated Product Brochure, “SP-Walker, short pneumatic walking brace”, Jan. 11, 2002.

International Preliminary Report of Patentability for International application No. PCT/US2012/032710 dated Oct. 17, 2013 from the International Bureau of WIPO.

Notification of Transmittal of International Search report and the Written Opinion of the International Searching Authority, or the Declaration, International Search Report and Written Opinion in International Application No. PCT/US2012/032710.

Australian Patent Examination Report No. 1 dated May 19, 2014, regarding AU Appln No. 2011285940.

* cited by examiner

ADJUSTABLE WALKING APPARATUS

CROSS-REFERENCE TO RELATED APPLICATION(S)

This application U.S. Ser. No. 15/336,650, filed on Oct. 27, 2016 is a continuation based on U.S. Ser. No. 14/789,918, now U.S. Pat. No. 9,510,965, issued on Dec. 6, 2016, which claims priority from U.S. Ser. No. 62/019,839, filed on Jul. 1, 2014 are incorporated by reference in their entirety.

BACKGROUND

Field

The present disclosure relates generally to orthopedic walking boots.

Background

It is common that people, especially active and/or frail people, experience a variety of lower leg and ankle injuries. To aid in the treatment of the injuries it is desirable to immobilize the injury, typically above and below the affected joint.

Physicians traditionally place a patient's leg in a short leg cast, which is a cast that usually begins at the patient's toes and ends below the patient's knee. Generally, casts retain heat, cause an itching sensation on the skin, and rub against the leg particularly after swelling of the leg subsides.

An alternative to the short leg cast is an orthopedic walking boot, or a premanufactured orthopedic walking boot, that is made of a rigid plastic frame lined with a soft component (e.g, a soft padding or a soft good) to accommodate the leg comfortably. Often, the liner, or soft component, may house a series of air bladders that can be adjusted by the patient to improve the fit and help compress the swelling to reduce pain and increase stability. The orthopedic walking boots can be removed to treat skin problems, such as, to remove sutures or conduct passive range of motion exercises. Short leg casts do not offer the luxury of easy on/off, and the cost associated with applying another cast after removal.

An orthopedic walking boot is primarily a rigid encasing that usually envelopes the leg and immobilizes the foot and ankle at a neutral position (e.g., the foot extends 90 degrees relative to the leg). The patient can walk easiest if the ankle is fixed at 90 degrees. At angles other than 90 degrees the patient will be walking on the toes or on the heel thereby altering the gait pattern of the patient. The outer sole of the foot is generally curved from front to back in a rocker bottom fashion. The curvature of the outer sole provides a smoother stride from front to back allowing the heel to strike the ground first, followed by a rocking of foot forward, and finally a push off on the toes for a successful step.

SUMMARY

In accordance with certain aspects of the present disclosure a walking apparatus is provided that includes a sole configured with an adjustable length, a heel portion, a forefoot portion operatively coupled to the heel portion, the forefoot portion configured for adjustment from a first position to at least one other position relative to the heel portion, wherein a length of the sole is configured to adjust from a first length to a second length when the forefoot portion is adjusted from the first position to the at least one other position.

Another aspect of the present disclosure provides a walking apparatus kit that includes a base, a heel portion including a first tread portion, a plurality of forefoot portions each configured with a different length and a second tread portion, each of the plurality of forefoot portions configured for individual coupling to the heel portion, wherein when one of the plurality of forefoot portions is coupled to the heel portion, the first tread portion and the second tread portion form a sole.

In accordance with certain aspects of the present disclosure, a method of adjusting a length of a walking apparatus is provided that includes activating an actuation mechanism located on a walking apparatus, and adjusting a length of the walking apparatus to conform to one or more predetermined parameters related to a user upon activation of the actuation mechanism.

In accordance with certain aspects of the present disclosure, a walking apparatus in provided that includes a sole having an adjustable length, the sole comprising a heel portion, a forefoot portion operatively coupled to the heel portion, the forefoot portion configured for adjustment from a first position to at least one other position, wherein a width of the sole is configured to adjust from a first width to a second width when the forefoot portion is adjusted from the first position to the at least one other position.

DETAILED DESCRIPTION

Figure 1A:
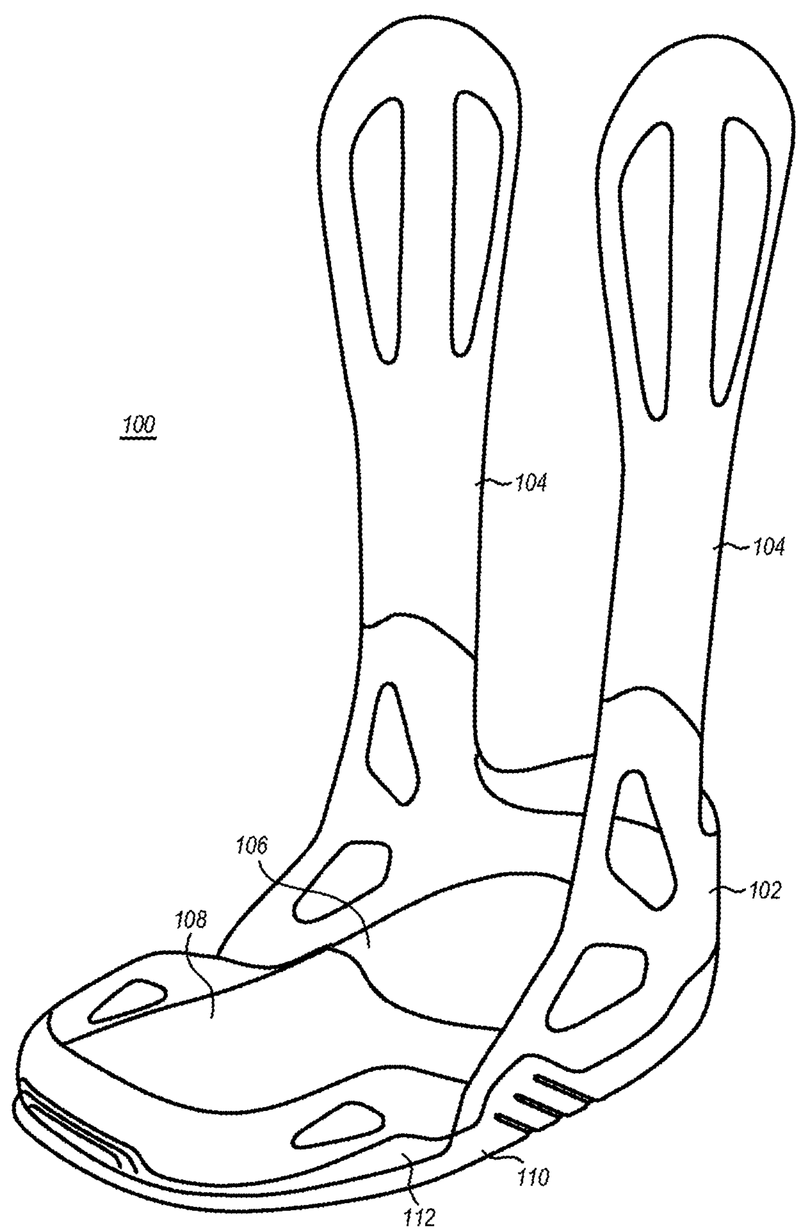
FIGS. 1A-1D illustrate a side perspective view of a walking apparatus in accordance with certain aspects of the present disclosure.

Various aspects of the present disclosure will be described herein with reference to drawings that are schematic illustrations of idealized configurations of the present disclosure. As such, variations from the shapes of the illustrations as a result, for example, manufacturing techniques and/or tolerances, are to be expected. Thus, the various aspects of the present invention presented throughout this description should not be construed as limited to the particular shapes of elements (e.g., regions, layers, sections, substrates, etc.) illustrated and described herein but are to include deviations in shapes that result, for example, from manufacturing. Thus, the elements illustrated in the drawings are schematic in nature and their shapes are not intended to illustrate the precise shape of an element and are not intended to limit the scope of the present invention, unless intentionally described as such.

It will be understood that when an element such as a region, layer, section, or the like, is referred to as being "on" another element, it can be directly on the other element or intervening elements may also be present. In contrast, when an element is referred to as being "directly on" another element, there are no intervening elements present. It will be further understood that when an element such as a structure is referred to as being coupled to another element, it can be directly connected to the other element or intervening elements may also be present. Similarly, two elements may be mechanically coupled by being either directly physically connected, or intervening connecting elements may be present. It will be further understood that when an element is referred to as being "formed" on another element, it can be deposited, attached, connected, coupled, or otherwise prepared or fabricated on the other element or an intervening element.

Furthermore, relative terms, such as "lower" or "bottom" and "upper" or "top," may be used herein to describe one element's relationship to another element as illustrated in the drawings. It will be understood that relative terms are intended to encompass different orientations of an apparatus in addition to the orientation depicted in the drawings. By way of example, if the orientation of an orthopedic walking boot shown in the drawings is turned over, elements described as being on the "lower" side of other elements would then be oriented on the "upper" side of the other elements. The term "lower", can therefore, encompass both an orientation of "lower" and "upper," depending of the particular orientation of the orthopedic walking boot. Similarly, if the orientation of an orthopedic walking boot shown in the drawing is turned over, elements described as "below" or "beneath" other elements would then be oriented "above" the other elements. The terms "below" or "beneath" can, therefore, encompass both an orientation of above and below.

Unless otherwise defined, all terms (including technical and scientific terms) used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the relevant art and this disclosure.

It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. The term "and/or" includes any and all combinations of one or more of the associated listed items.

The detailed description set forth below in connection with the appended drawings is intended as a description of various aspects of the present disclosure and is not intended to represent all aspects in which the present invention may be practiced. The detailed description includes specific details for the purpose of providing a thorough understanding of the present invention. However, it will be apparent to those skilled in the art that the present invention may be practiced without these specific details. In some instances, well-known structures and components are shown in block diagram form in order to avoid obscuring the concepts of the present disclosure.

Various aspects of the present disclosure may provide a walking apparatus with an adjustable length and/or width that may be fitted around the leg to provide support and allow ambulation for an affected limb.

People often experience injuries to the lower leg and ankle. For example, blunt trauma, sports injuries and common falls are the primary causes. Injuries such as fractures of the bones or soft tissue injuries (e.g., ligamentous tears) have similar symptoms. Swelling, pain and inability to ambulate without support are expected and predictable. Some injuries need to be immobilized for a period of time for the injury to heal. The time required for ligamentous injuries to heal is similar to the time required for fractures to heal. A period of 4 to 6 weeks of immobilization is common. Different injuries require different rehab times and regimes.

Aspects of the present disclosure are directed to a walking apparatus (e.g., an orthopedic walking boot) with an adjustable length and/or width to accommodate a variety of foot sizes and swelling. In an aspect of the prevention disclosure, an orthopedic walking boot may include bilateral struts which connect a base of the orthopedic walking boot to an upper portion of the orthopedic walking boot. The struts may be rigid and provided on either side of the leg. The bilateral struts may be held onto the limb with strapping systems that encircle at least a portion of the limb. In another aspect, the base may be attached to a posterior piece which extends from the foot to the back of the leg and calf forming a clamshell configuration. In the clamshell configuration, a single piece encompasses a portion of the side of the leg (similar to the bilateral configuration) as well as the rear of the leg. The orthopedic walking boot may include an adjoining anterior piece that joins or overlaps the posterior piece and is held on by a traditional strapping system or with one or more mechanical attachment mechanisms. In another aspect, the orthopedic walking boot may comprise a "hybrid" configuration (also referred herein as a "multi-sectioned" configuration). In the hybrid configuration, the base may be attached to the bilateral struts of the bilateral configuration and also attached a separate/non-integral posterior element that encompasses the rear of leg (similar to the rear portion of the clamshell). In this manner, the bilateral struts surround the side of the legs while the separate posterior portion encompasses the rear of the leg. Thus, the hybrid configuration achieves a similar result as the clamshell with multiple sections, hence, "multi-sectioned."

According to one aspect of the present disclosure, the orthopedic walking boot may be configured such that the portion that receives the user's foot (e.g., the base portion) extends at a 90° angle or at substantially 90° relative to a longitudinal axis of the portion that receives the user's leg (e.g., the upper portion). In another aspect, the orthopedic walking boot may include two struts rising from the base. The orthopedic walking boot may further include a soft component within the constraints of the struts and on top of the base. The soft component may be held by straps.

The orthopedic walking boot may include a base portion that is adjustable in length and/or width, in accordance with one aspect of the present disclosure. Traditionally, a hospital, clinic, or orthopedic supply company have had to stock orthopedic walking apparatuses such as walking boots and post-operative shoes in variety of sizes to accommodate users with different foot sizes. Certain foot sizes are more common than others, and a hospital, clinic, or orthopedic supply company may run out of those sizes more quickly causing the stock room to contain a surplus of certain sizes and a dearth of others.

Furthermore, there is a growing awareness that manufacturing fewer versions of a product can increase revenue for the manufacturer. For example, manufacturing a walking apparatus all of one type that can accommodate all foot sizes can reduce the number of parts and/or equipment required during the manufacturing process, and also reduce the amount of material needed to produce the walking apparatus.

In an effort to reduce the number of sizes that a supplier is required to carry and the manufacturer is required to produce, certain aspects of the present disclosure include a walking apparatus that is configured with an adjustable length and/or width. An adjustable walking apparatus can ensure that as long as the product is in stock, the majority of patients will be able to be fitted with the walking apparatus regardless of foot length, width, or amount of swelling since each apparatus can be specifically fitted to an individual patient. Consequently, the adjustable walking apparatus is able to provide a better fit and support.

As discussed above, an aspect of the present disclosure includes an orthopedic walking boot with an outer sole that is adjustable in length. FIGS. 1A-1D each illustrate an adjustable orthopedic walking boot 100 with an outer sole which may be made up of multiple sections 110, 112 and overmolded to the base 102 of the orthopedic walking boot 100. Each section of the outer sole 110, 112 may be formed of an elastomeric material, and the elastomeric material of the first section 110 may be the same or different than the elastomeric material of the section 112. The orthopedic walking boot 100 may include a support assembly made up of bilateral struts 104. However, the adjustable orthopedic walking boot may alternatively have support assemblies consistent with the clamshell or hybrid types discussed above.

FIGS. 1A-1D each illustrate one aspect of the present disclosure in which an adjustable orthopedic walking boot 100 with a bilateral struts 104 support system includes a base 102 made up of a heel portion 106 and an adjustable forefoot portion 108. FIG. 1A shows the adjustable orthopedic walking boot 100 in a non-extended configuration. The outer sole can completely cover the bottom surface of the base 102 and be made up of a first section 110 and a second section 112. In particular the first section 110 of the outer sole can cover the heel portion 106 of the base 102, while the second section 112 of the outer sole can cover the forefoot portion 108 of the base 102. As seen in the illustration, the second section 112 of the outer sole can remain behind the first section 110 of the outer sole when the forefoot portion 108 is in a non-extended position with respect to the heel portion 106. Moreover, the outer sole may extend up the sides of the perimeter of the walker base 102 to maximize surface contact between the outer sole and the base 102. In an aspect, the outer sole may comprise a thermoplastic elastomer bonded by overmolding to the base 102. The base 102 may comprise a rigid polypropylene material. Alternatively, a number of different material pairs may be bonded in a similar manner, as long as they are chemically and thermally compatible. The bottom surface of both of the first section 110 and the second section 112 of the outer sole may include tread formed during the overmolding process. Various tread patterns may be applied by using a series of inserts in the overmold tool, where each insert is designed aesthetically or otherwise, to provide a different appearance of the tread while maintaining the desired physical properties, e.g., water channeling, grip on slippery surfaces, etc. Furthermore, the longitudinal axis of the outer sole may be defined as the axis along the direction from the heel of the outer sole to the toe/forefoot of the outer sole.

Figure 1B:
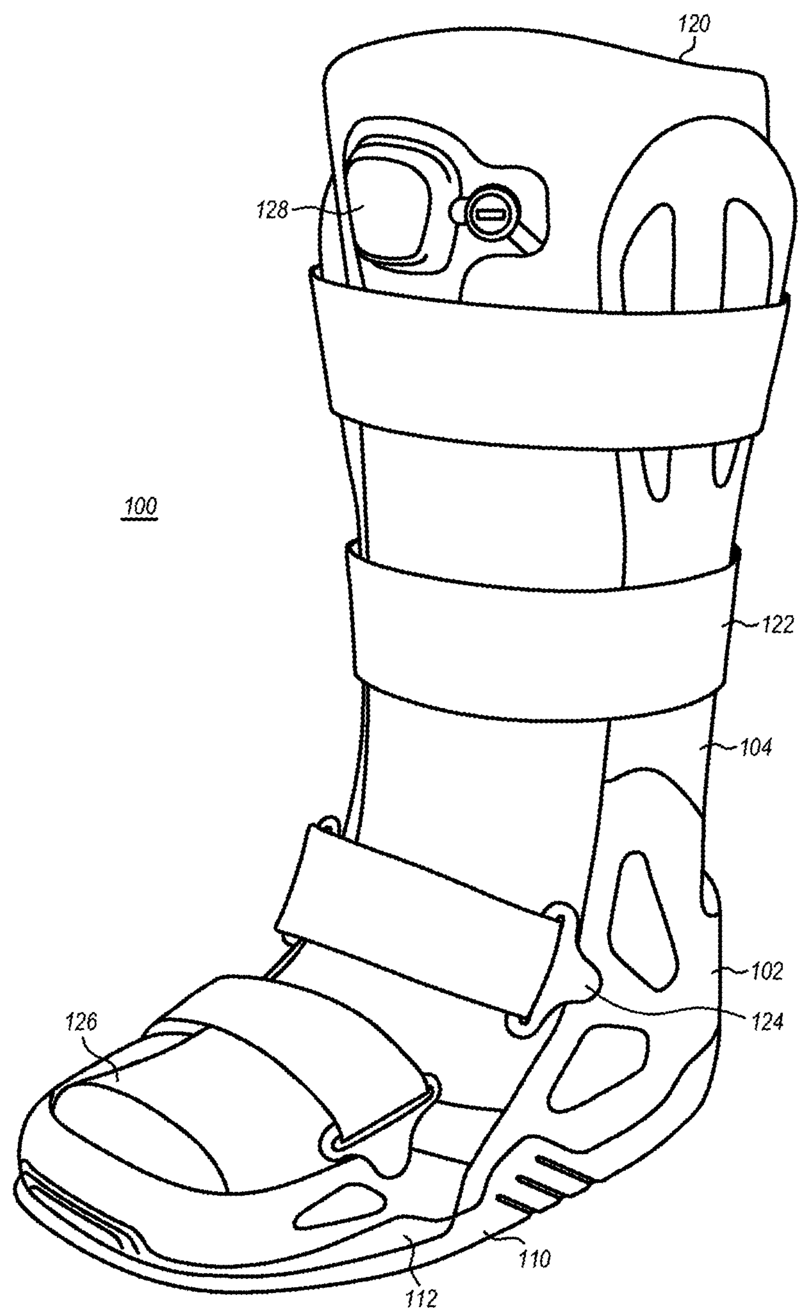

FIG. 1B shows a similar adjustable orthopedic walking boot 100 as illustrated in FIG. 1A, but with the adjustable orthopedic walking boot 100 further including a soft component 122 positioned within the constraints of the struts 104 and on top of the base 102 of the walking boot. The soft component 120 may be held in position by a plurality of straps 122 that operatively couple to the base 102 with coupling members 124. Alternatively, the straps 122 can operatively couple to the base 102 and the struts 104 using a hook-and-eye type fastener, an adhesive, or a tying member. Furthermore, the soft component can include a gap 126 proximal to the forward most position of the forefoot portion 108 that allows for air-flow to the user's toes and/or feet while in the soft component 120. Alternately, the soft component 120 can include be configured so that there is no gap 126, but instead has a closed end surface that can provides additional protection to a user's toes.

Figure 1C:
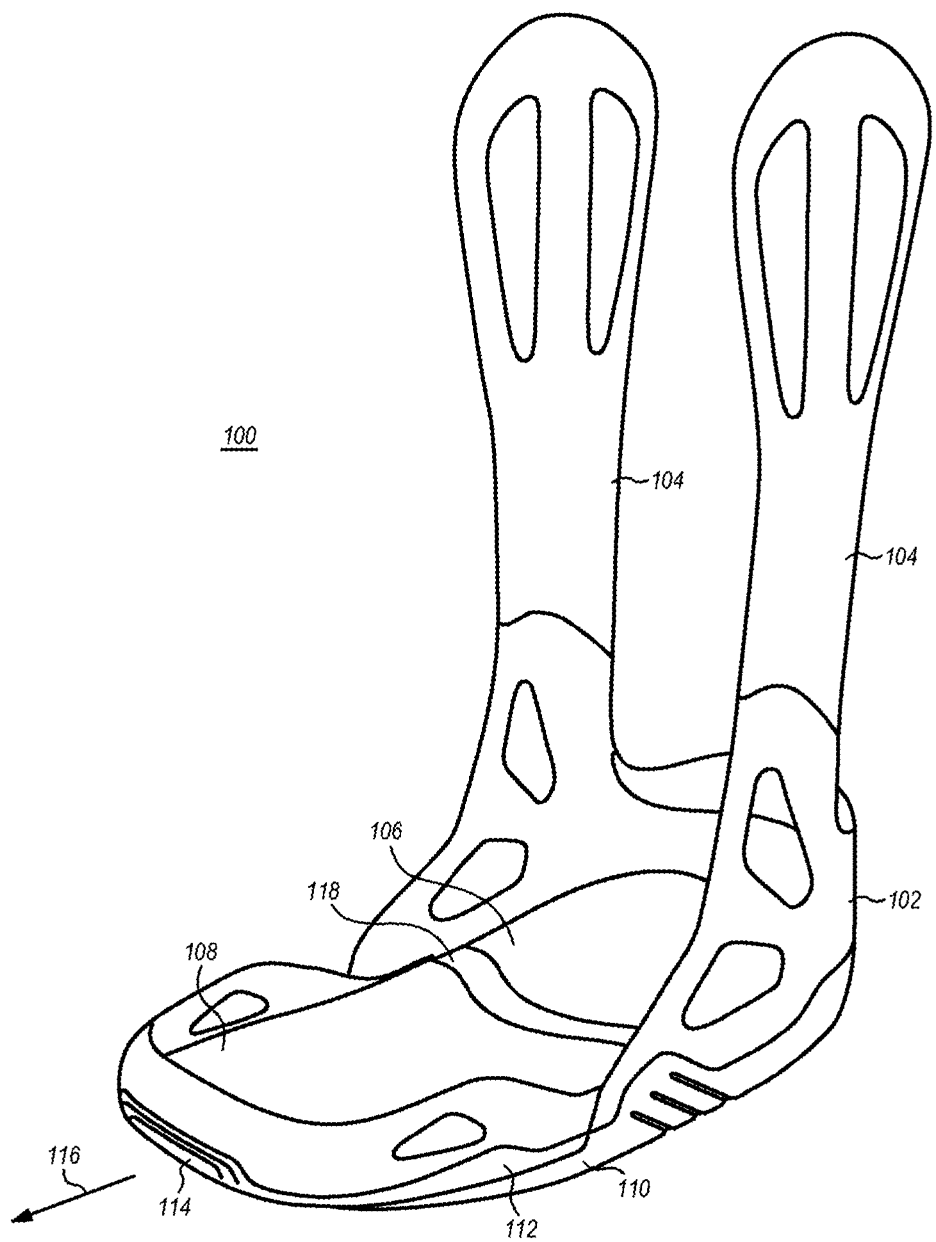

FIG. 1C illustrates the adjustable walking boot of FIG. 1A but in the extended position. More specifically, the forefoot portion 108 is illustrated as being adjusted from a first position (e.g., non-extended position) to a second position (e.g., extended position) with respect to the heel portion 106. When the forefoot portion 108 is adjusted or moved from the first position to the second position, a section 114 of the second portion 112 of the outer sole moves from behind the first portion 110 of the outer sole thereby effectively extending the length of the outer sole from a first length (e.g., non-extended position) to a second length (e.g., extended position). The adjustment is illustrated by arrow 116 and can create a separation gap 118 between the forefoot potion 108 and the heel portion 106 on an inner surface of the walking boot 100. Although not illustrated, the exposed section 114 may include a lip or terraced portion that is configured to mate with a forward most edge of the first portion 110 of the outer sole to provide a smooth transition between the exposed section 114 of the second portion 112 of the outer sole and the first portion 110 of the outer sole. Such a configuration can provide an even walking surface for the user, thereby increasing the stability of the walking boot 100. Conversely, when the forefoot potion 108 is adjusted from the extended position back to the non-extended position, the exposed section 114 of the second portion 112 of the outer sole retracts behind the first portion 110 of the outer sole thereby effectively shortening the length of the outer sole.

Figure 1D:
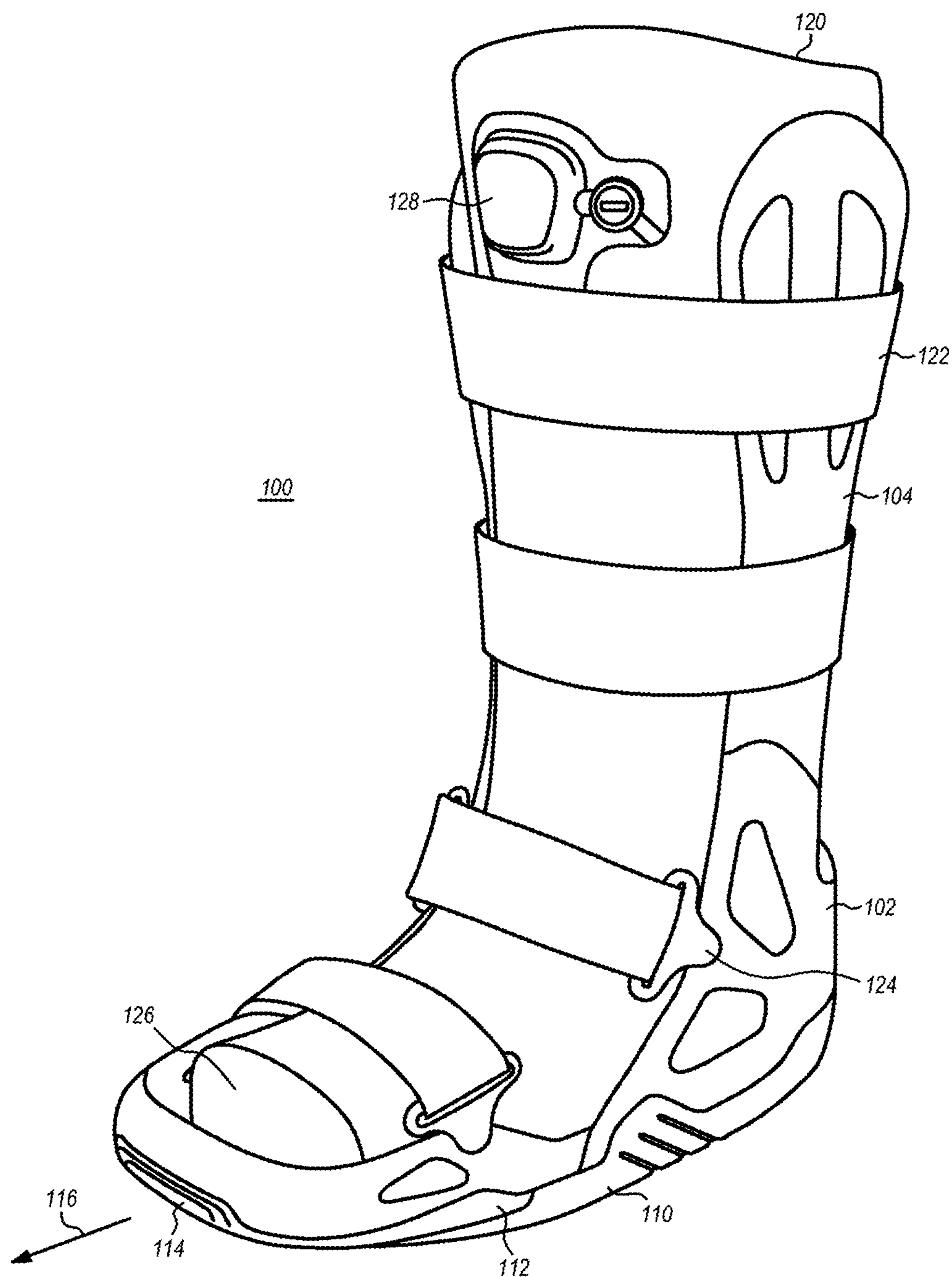

FIG. 1D shows the same adjustable walking boot with the soft component 122 as depicted in FIG. 1B but with the forefoot portion 108 in the extended position as illustrated in FIG. 1C.

Figure 2A:
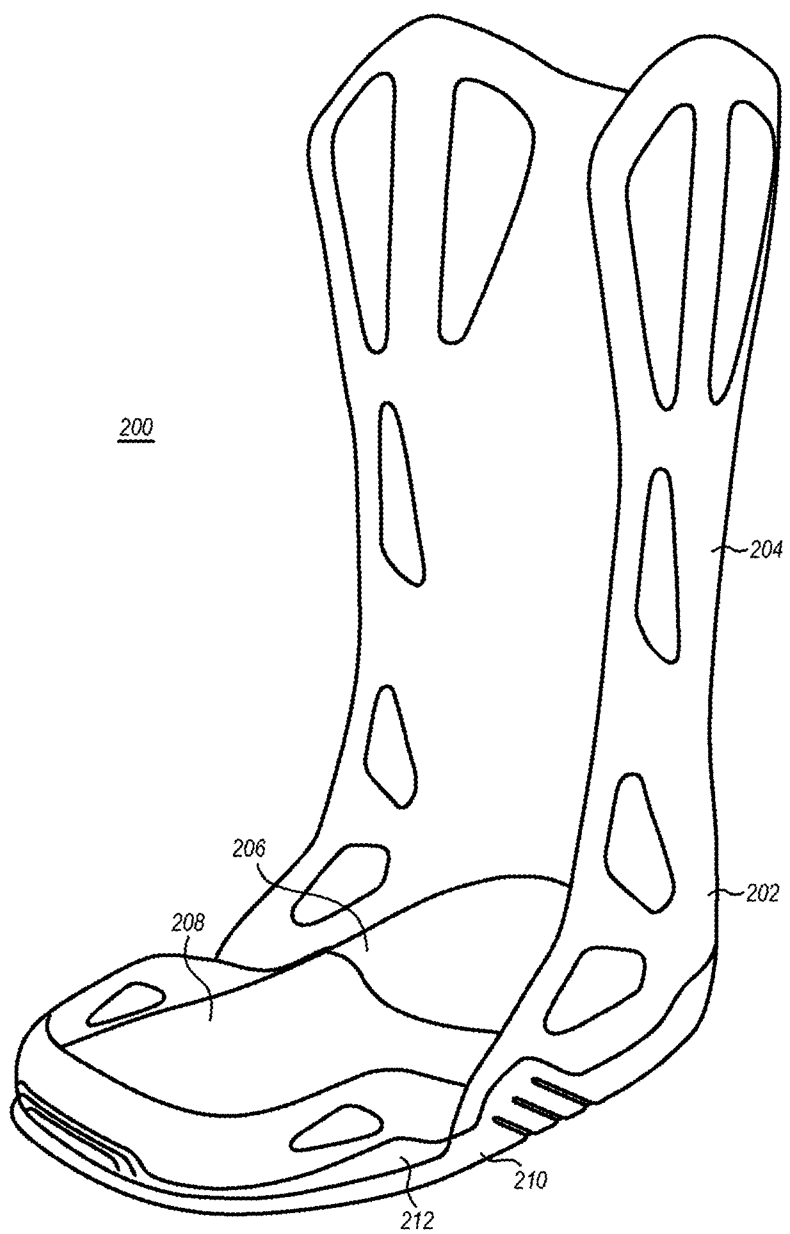
FIGS. 2A-2F illustrate a side perspective view of a walking apparatus in accordance with certain aspects of the present disclosure.

FIGS. 2A-2D each illustrate one aspect of the present disclosure in which an adjustable orthopedic walking boot 200 includes a clamshell support 204 and a base 202 made up of a heel portion 206 and an adjustable forefoot portion 208. FIG. 2A depicts the adjustable orthopedic walking boot 200 in a non-extended configuration. The outer sole can completely cover the bottom surface of the base 202 and be made up of a first section 210 and a second section 212. In particular the first section 210 of the outer sole can cover the heel portion 206 of the base, while the second section 212 of the outer sole can cover the forefoot portion 208 of the base 202. As seen in the illustration, the second section 212 of the outer sole can remain behind the first section 210 of the outer sole when the forefoot portion 208 is in a non-extended position with respect to the heel portion 206. Moreover, the outer sole may extend up the sides of the perimeter of the walker base 202 to maximize surface contact between the outer sole and the base 202. In an aspect, the outer sole may comprise a thermoplastic elastomer bonded by overmolding to the base 202. The base 202 may comprise a rigid polypropylene material. Alternatively, a number of different material pairs may be bonded in a similar manner, as long as they are chemically and thermally compatible. The bottom surface of both of the first section 210 and the second section 212 of the outer sole may include tread formed during the overmolding process. Various tread patterns may be applied by using a series of inserts in the overmold tool, where each insert is designed aesthetically or otherwise, to provide a different appearance of the tread while maintaining the desired physical properties, e.g., water channeling, grip on slippery surfaces, etc. Furthermore, the longitudinal axis of the outer sole may be defined as the axis along the direction from the heel of the outer sole to the toe/forefoot of the outer sole.

Figure 2B:
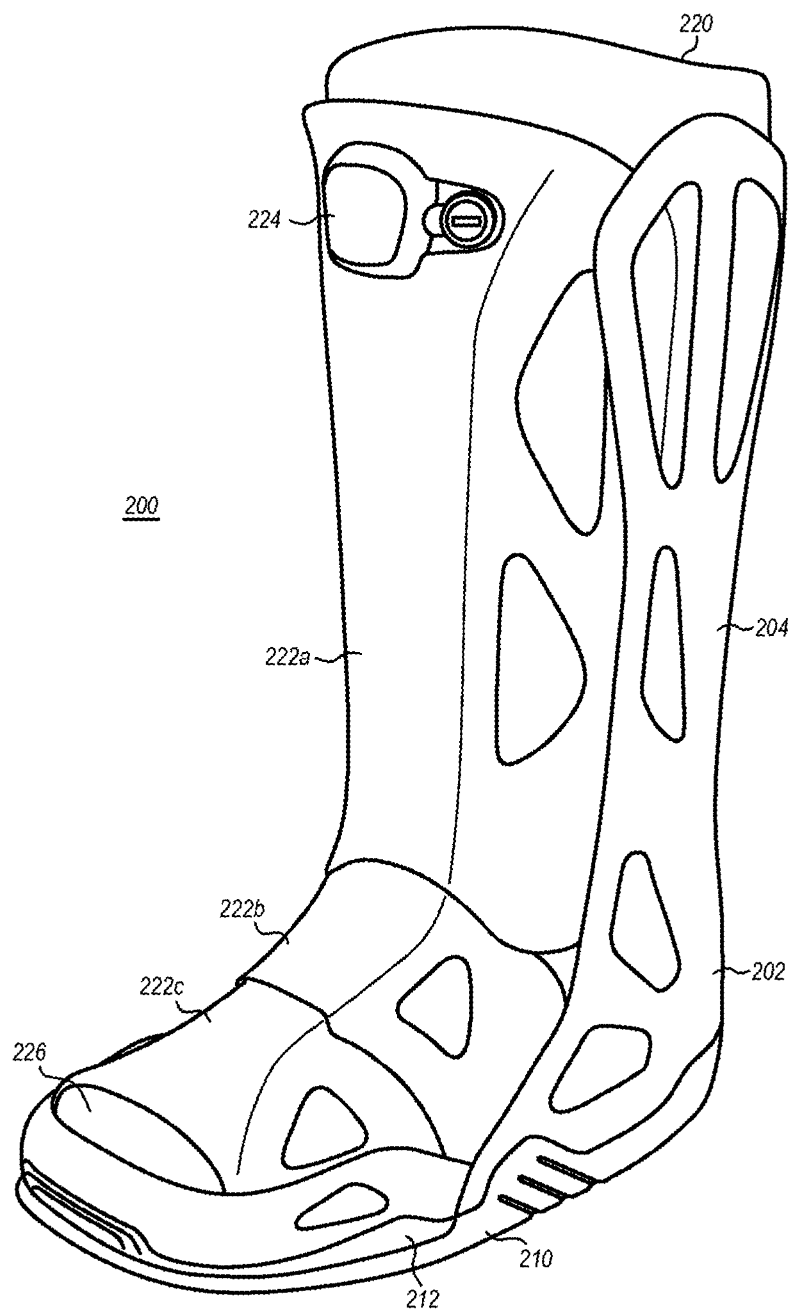
Figure 2C:
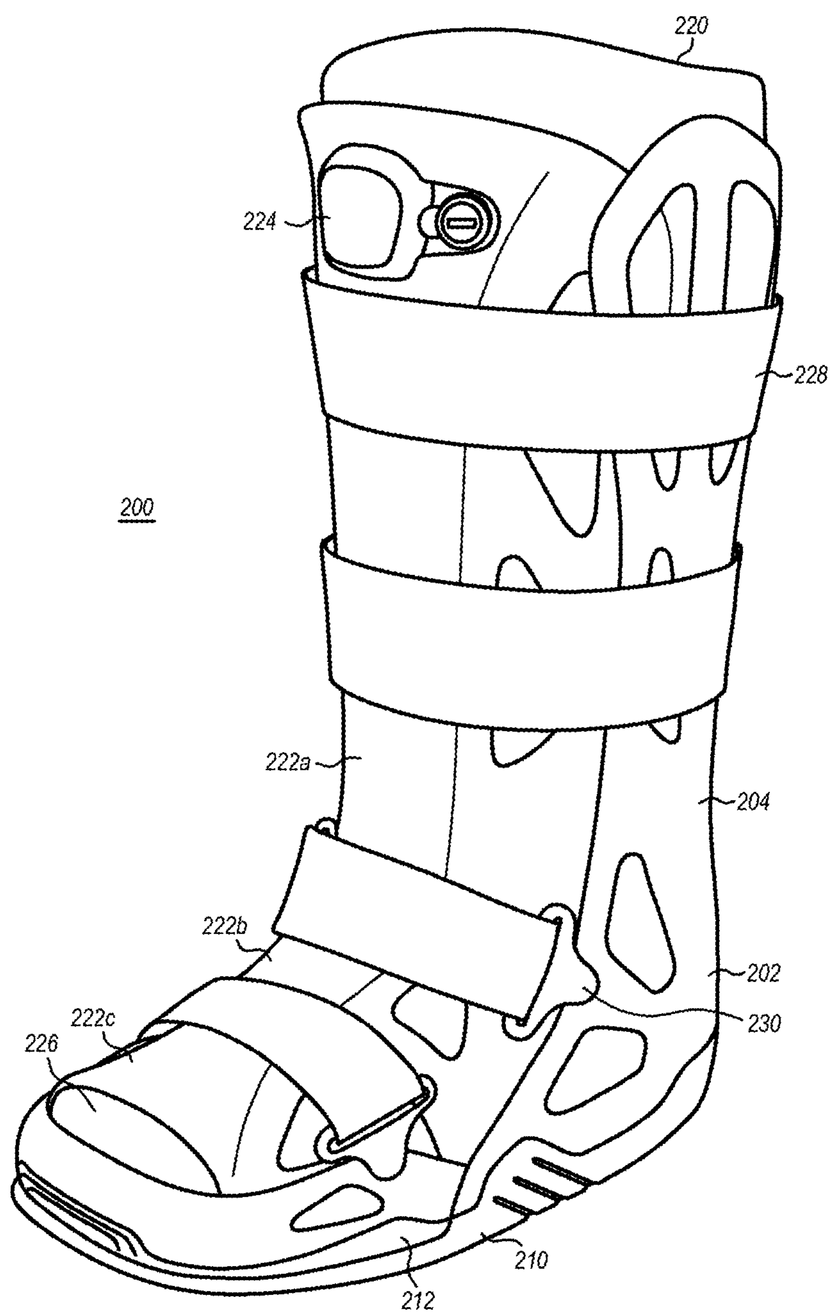

FIG. 2B shows a similar adjustable orthopedic walking boot 200 as illustrated in FIG. 2A, but with the adjustable orthopedic walking boot 200 further including a soft component 220 positioned within the constraints of the clamshell support 204 and on top of the base 102 of the walking boot. FIG. 2B further illustrates anterior plates 222*a*, 222*b*, 222*c* that are positioned over the soft component 220 and can be used to provide additional protection/support to the anterior portion of a user's foot and/or leg when in the walking boot 200. Although three anterior plates are depicted in FIGS. 2B and 2C, it is understood that more or fewer anterior pieces can be used without departing from the scope of the present disclosure. The soft component 220 and anterior plates 222*a*, 222*b*, 222*c* can be configured such that a gap 226 can be formed proximal to the forward-most position of the forefoot portion 208 which can allow for air-flow to the user's toes and/or feet while in the soft component 220 and covered with the anterior plates 222*a*, 222*b*, 222*c*.

The soft component 220 and anterior plates 222*a*, 222*b*, 222*c* may be held in position by a plurality of straps 228, as illustrated in FIG. 2C, that operatively couple to the base 202 with coupling members 230. The straps 228 can operatively couple to the base 202 and the clamshell support 204 using a hook-and-eye type fastener, an adhesive, a tying member, or any other type of coupling mechanism as understood by one of ordinary skill in the art.

Figure 2D:
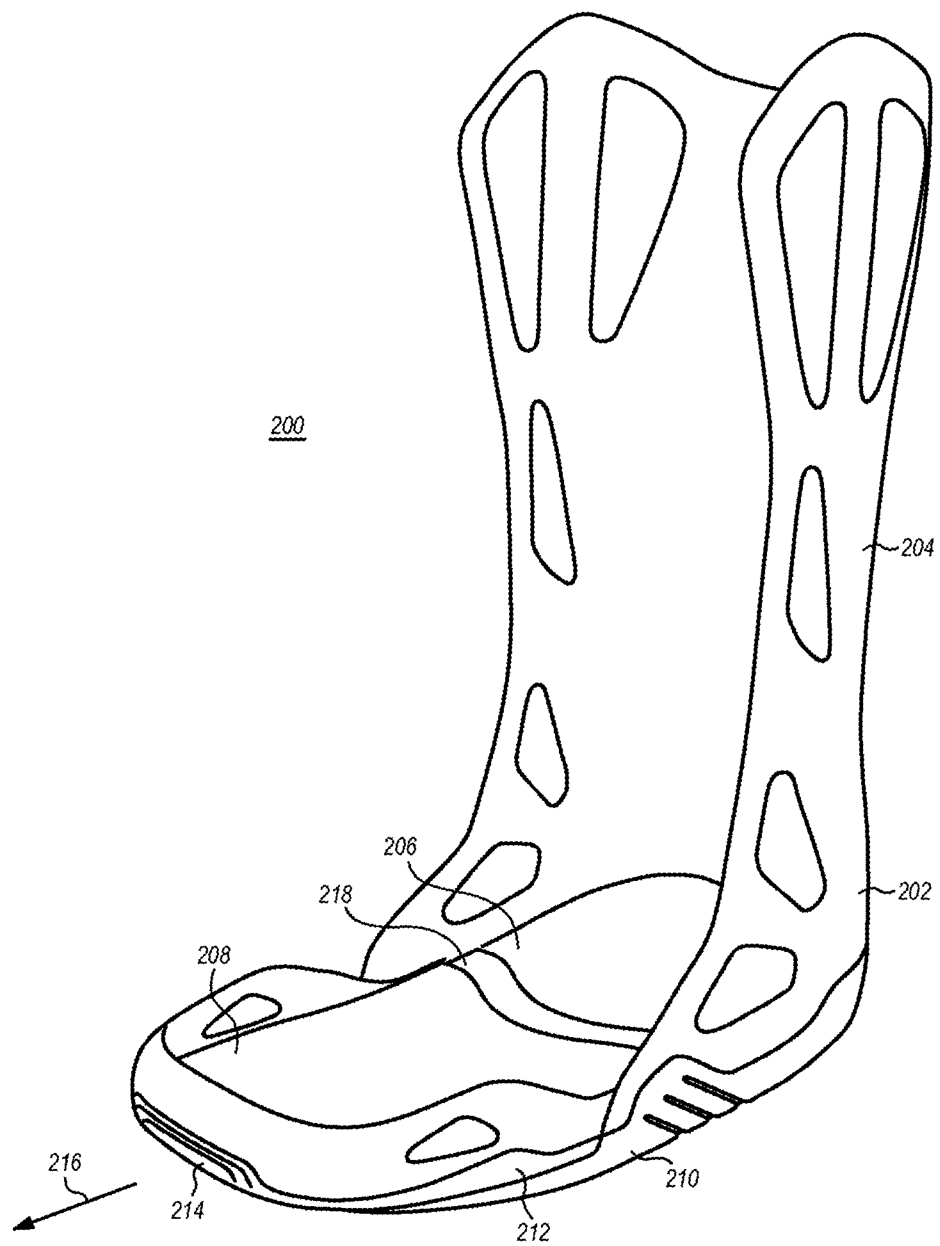

FIG. 2D illustrates the adjustable walking boot of FIG. 2A but depicted in the extended position. More specifically, the forefoot portion 208 is illustrated as being adjusted from a first position (e.g., non-extended position) to a second position (e.g., extended position) with respect to the heel portion 206. When the forefoot portion 208 is adjusted or moved from the first position to the second position, a section 214 of the second portion 212 of the outer sole moves from behind the first portion 210 of the outer sole thereby effectively extending the length of the outer sole from a first length (e.g., non-extended position) to a second length (e.g., extended position). The adjustment is illustrated by arrow 216 and can create a separation gap 218 between the forefoot potion 208 and the heel portion 206 on an inner surface of the walking boot 200. Although not illustrated, the exposed section 214 may include a lip or terraced portion that is configured to mate with a forward most edge of the first portion 210 of the outer sole to provide a smooth transition between the exposed section 214 of the second portion 212 of the outer sole and the first portion 210 of the outer sole. Such a configuration can provide an even walking surface for a user, thereby increasing the stability of the walking boot 200. Conversely, when the forefoot potion 208 is adjusted from the extended position back to the non-extended position, the exposed section 214 of the second portion 212 of the outer sole retracts behind the first portion 210 of the outer sole thereby effectively shortening the length of the outer sole.

Figure 2E:
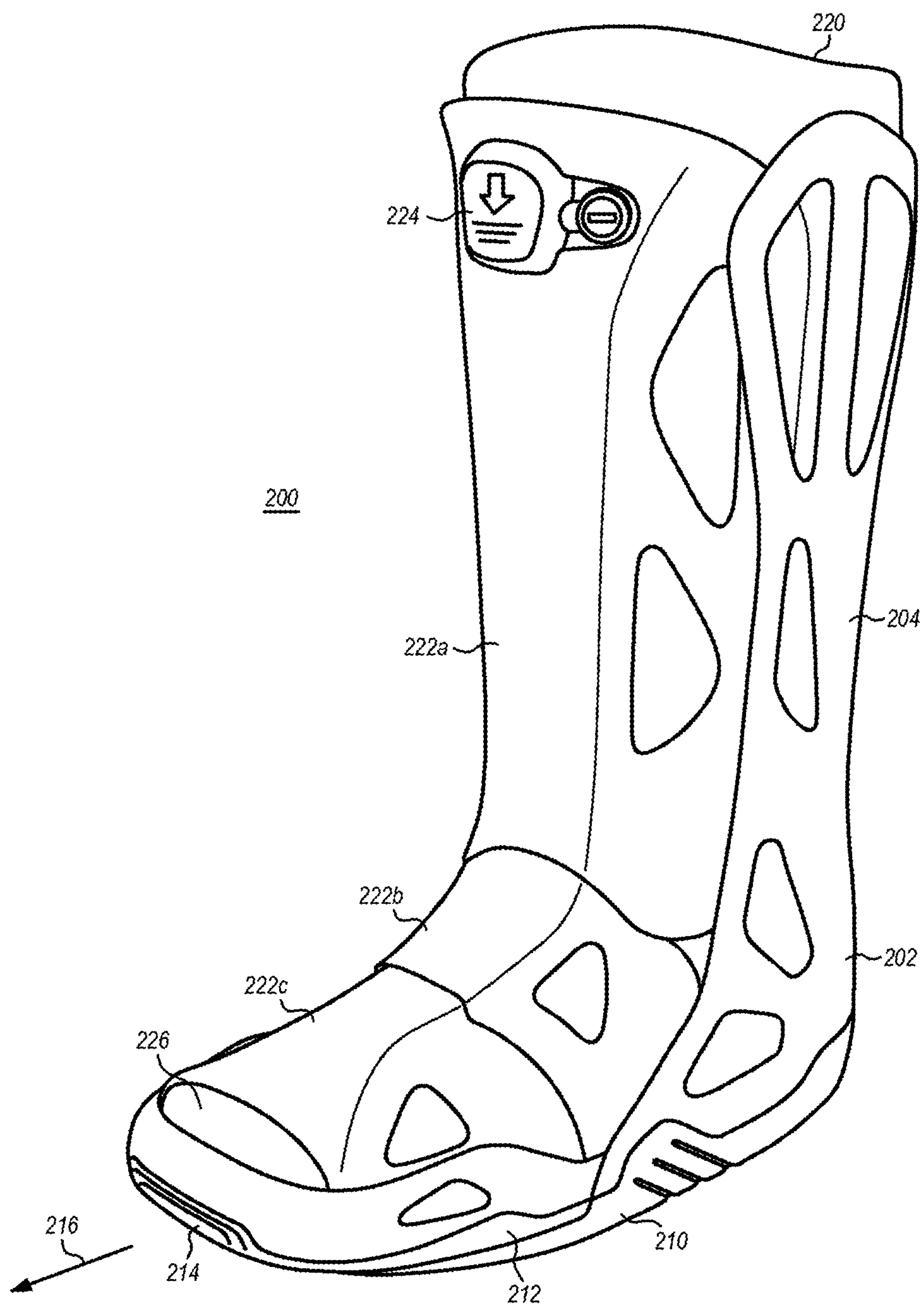
Figure 2F:
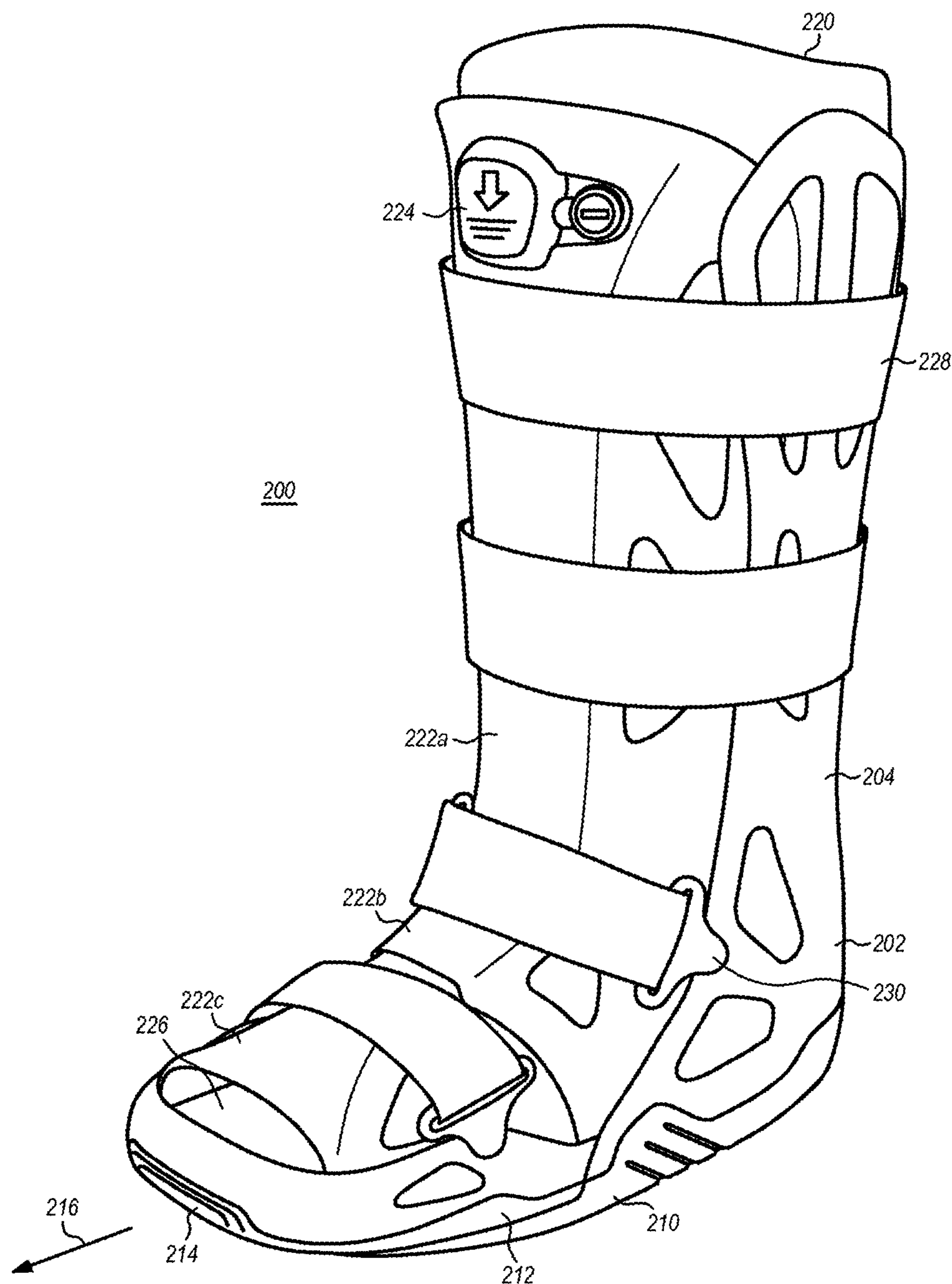

FIG. 2E shows the adjustable walking boot 200 with the soft component 220 and anterior plates 222*a*, 222*b*, 222*c* illustrated in FIG. 2B but depicted with the forefoot portion 208 in the extended position as illustrated in FIG. 2D. FIG. 2F depicts shows the adjustable walking boot 200 with straps 228 and coupling members 230 as depicted in FIG. 2C but with the forefoot portion 208 in the extended position as seen in FIG. 2D.

Figure 3A:
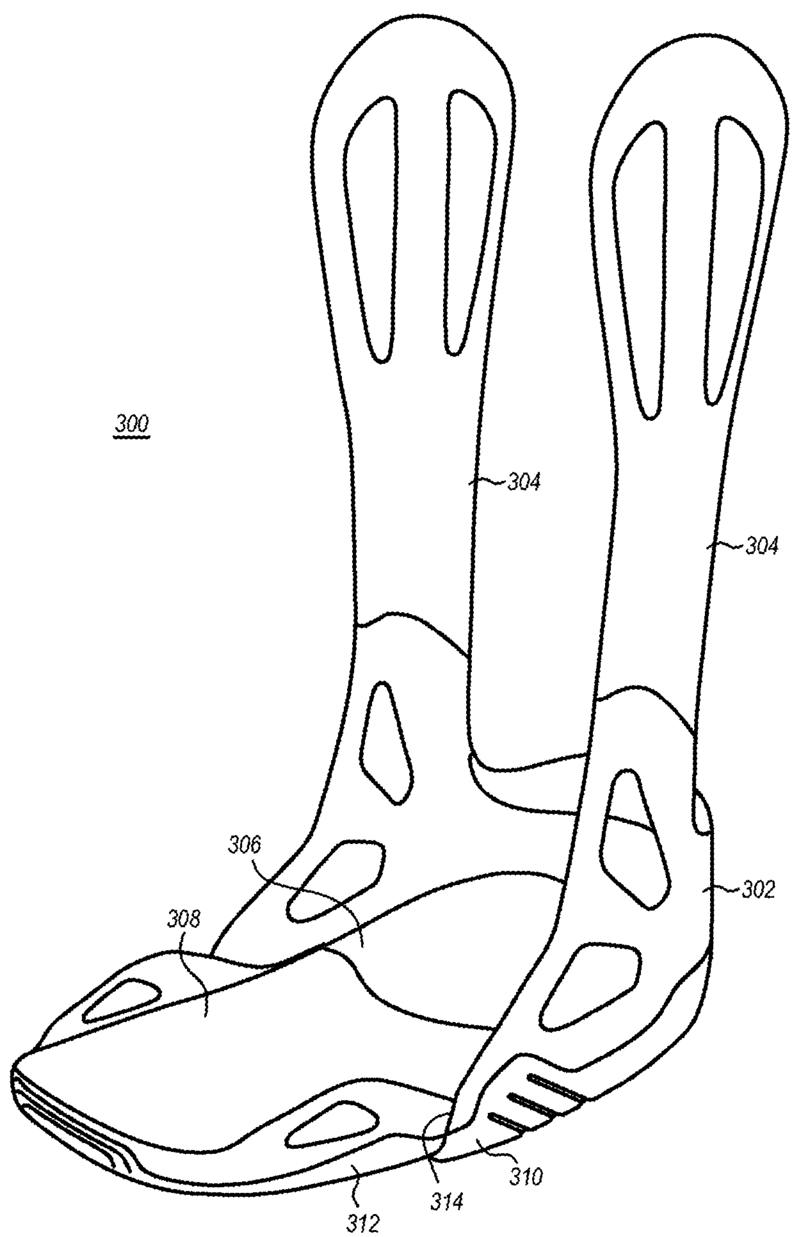
FIGS. 3A-3B illustrate a side perspective view of a walking apparatus in accordance with certain aspects of the present disclosure.
Figure 3B:
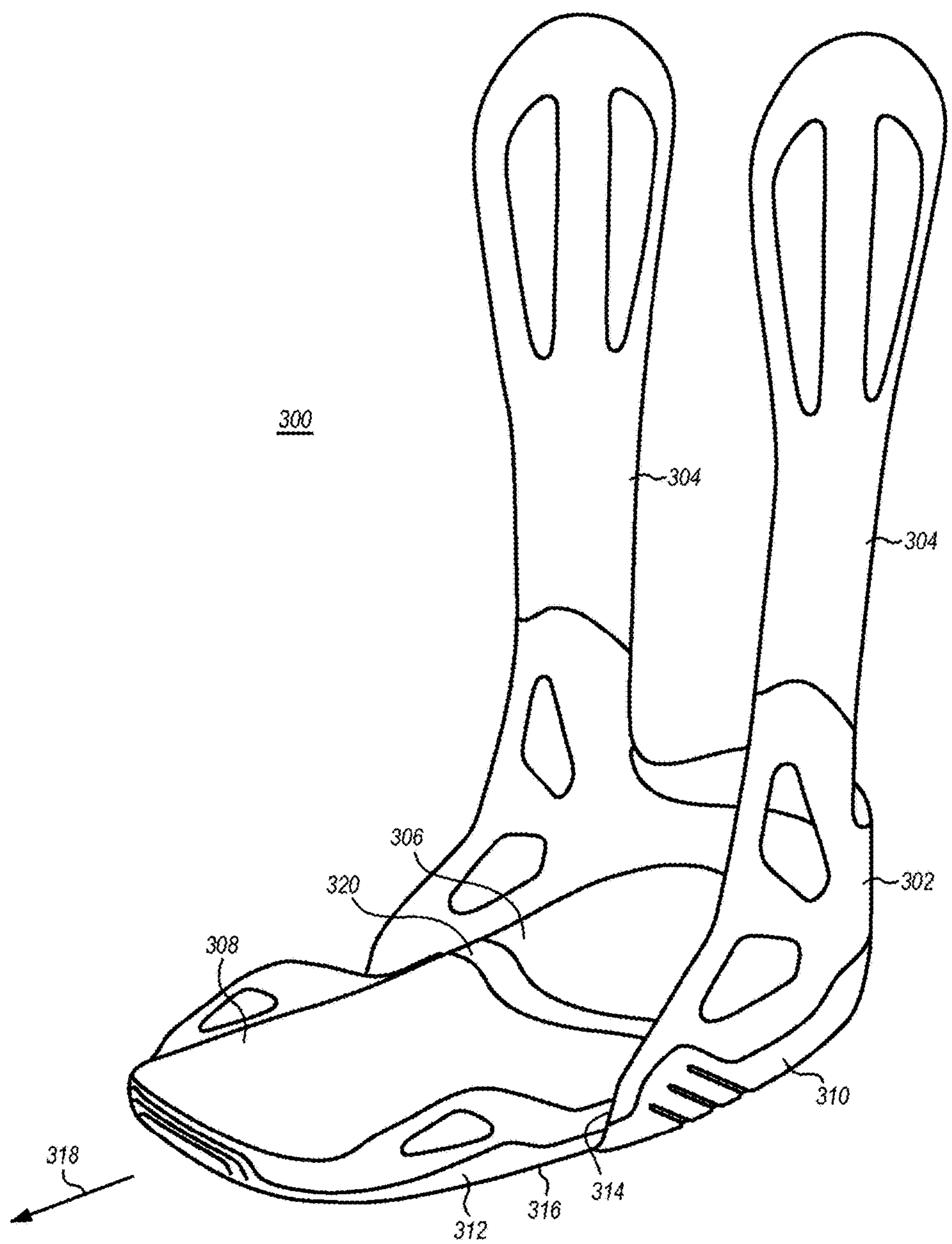

FIGS. 3A and 3B illustrate one aspect of the present disclosure in which an adjustable orthopedic walking boot 300 with a bilateral strut 304 support system that can include a base 302 made up of a heel portion 306 and an adjustable forefoot portion 308. FIG. 3A shows the adjustable orthopedic walking boot 300 in a non-extended configuration. The outer sole can completely cover the bottom surface of the base 302 and be made up of a first section 310 and a second section 312. In particular the first section 310 of the outer sole can cover the heel portion 306 of the base, while the second section 312 of the outer sole can cover the forefoot portion 308 of the base 302. As seen in the FIG. 3A, the entire second section 312 of the outer sole does not remain behind the first section 310 of the outer sole when the forefoot portion 308 is in a non-extended position with respect to the heel portion 306, as depicted in FIG. 1A. Instead, in the non-extended position, a break 314 in the outer sole proximal to a midsection of the base 302 can allow the first section 310 and at least a portion of the second section 312 of the outer sole to form the walking surface of the walking boot 300. Although the break 314 is illustrated as being near a midsection of the base 302, it is understood that the break 314 can be positioned anywhere along the longitudinal axis of the base 302 without departing from the scope of the present disclosure. Moreover, the outer sole may extend up the sides of the perimeter of the walker base 302 to maximize surface contact between the outer sole and the base 302. In an aspect, the outer sole may comprise a thermoplastic elastomer bonded by overmolding to the base 302. The base 302 may comprise a rigid polypropylene material. Alternatively, a number of different material pairs may be bonded in a similar manner, as long as they are chemically and thermally compatible. The bottom surface of both of the first section 310 and the second section 312 of the outer sole may include tread formed during the overmolding process. Various tread patterns may be applied by using a series of inserts in the overmold tool, where each insert is designed aesthetically or otherwise, to provide a different appearance of the tread while maintaining the desired physical properties, e.g., water channeling, grip on slippery surfaces, etc. Furthermore, the longitudinal axis of the outer sole may be defined as the axis along the direction from the heel of the outer sole to the toe/forefoot of the outer sole.

FIG. 3B illustrates the adjustable walking boot 300 of FIG. 3A but depicted in the extended position. More specifically, the forefoot portion 308 is illustrated as being adjusted from a first position (e.g., non-extended position) to a second position (e.g., extended position) with respect to the heel portion 306. When the forefoot portion 308 is adjusted or moved from the first position to the second position, a section 316 of the second portion 312 of the outer sole moves from behind the first portion 310 of the outer sole thereby effectively extending the length of the outer sole from a first length (e.g., non-extended position) to a second length (e.g., extended position). The adjustment is illustrated by arrow 318 and can create separation gap 320 between the forefoot potion 308 and the heel portion 306 on an inner surface of the walking boot 300. Although not illustrated, the exposed section 316 may include a lip or terraced portion that is configured to mate with a forward most edge of the first portion 310 of the outer sole to provide a smooth transition between the exposed section 314 of the second portion 312 of the outer sole and the first portion 310 of the outer sole. Such a configuration can provide an even walking surface for a user, thereby increasing the stability of the walking boot 300. Conversely, when the forefoot potion 308 is adjusted from the extended position back to the non-extended position, the exposed section 316 of the second portion 312 of the outer sole retracts behind the first portion 310 of the outer sole thereby effectively shortening the length of the outer sole.

Figure 4A:
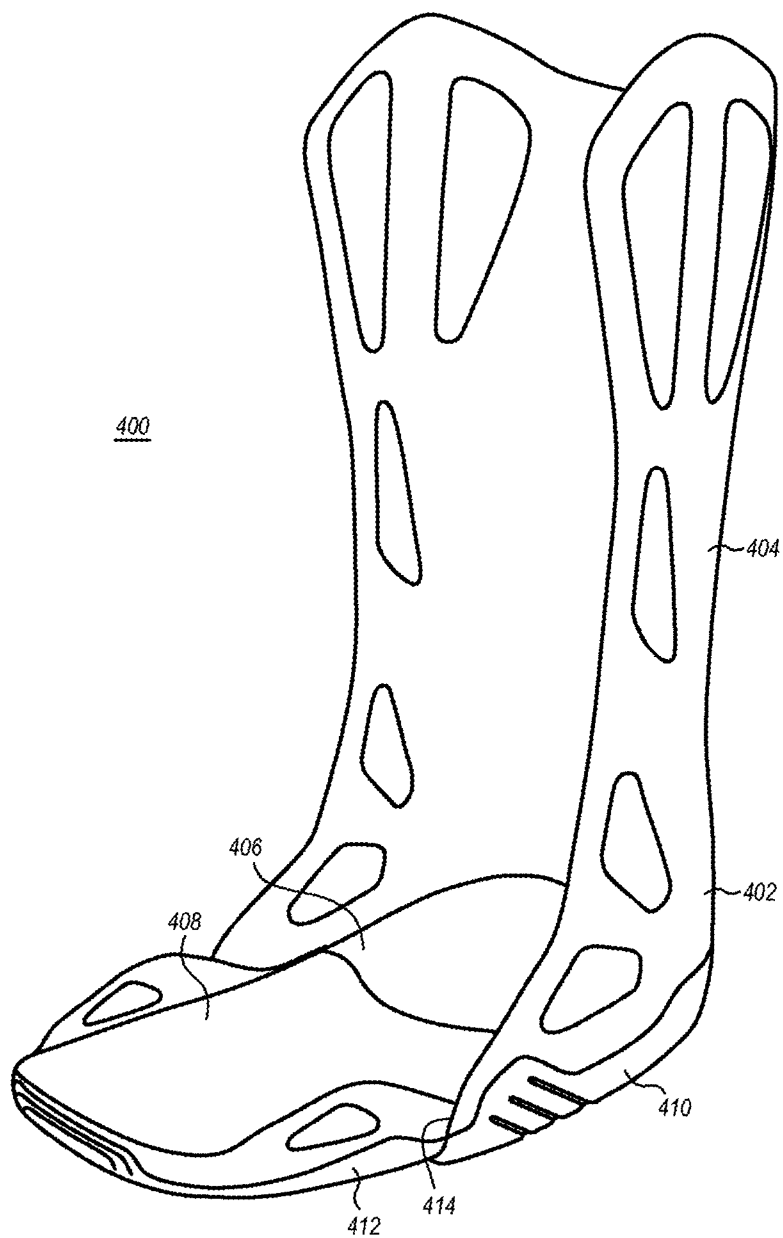
FIGS. 4A-4D illustrate a side perspective view of a walking apparatus in accordance with certain aspects of the present disclosure.

FIGS. 4A-4D illustrate one aspect of the present disclosure in which an adjustable orthopedic walking boot 400 includes a clamshell support 404 and a base 402 made up of a heel portion 406 and an adjustable forefoot portion 408. FIG. 4A shows the adjustable orthopedic walking boot 400 in a non-extended configuration. The outer sole can completely cover the bottom surface of the base 402 and be made up of a first section 410 and a second section 412. In particular the first section 410 of the outer sole can cover the heel portion 406 of the base 402, while the second section 412 of the outer sole can cover the forefoot portion 408 of the base 402. As seen in the FIG. 4A, the entire second section 412 of the outer sole does not remain behind the first section 410 of the outer sole when the forefoot portion 408 is in a non-extended position with respect to the heel portion 406, as depicted in FIG. 2A. Instead, in the non-extended position, a break 414 in the outer sole proximal to a midsection of the base 402 can allow the first section 410 and at least a portion of the second section 412 of the outer sole to form the walking surface of the walking boot 400. Although the break 414 is illustrated as being near a midsection of the base 402, it is understood that the break 414 can be positioned anywhere along the longitudinal axis of the base 402 without departing from the scope of the present disclosure. Moreover, the outer sole may extend up the sides of the perimeter of the walker base 402 to maximize surface contact between the outer sole and the base 402. In an aspect, the outer sole may comprise a thermoplastic elastomer bonded by overmolding to the base 402. The base 402 may comprise a rigid polypropylene material. Alternatively, a number of different material pairs may be bonded in a similar manner, as long as they are chemically and thermally compatible. The bottom surface of both of the first section 410 and the second section 412 of the outer sole may include tread formed during the overmolding process. Various tread patterns may be applied by using a series of inserts in the overmold tool, where each insert is designed aesthetically or otherwise, to provide a different appearance of the tread while maintaining the desired physical properties, e.g., water channeling, grip on slippery surfaces, etc. Furthermore, the longitudinal axis of the outer sole may be defined as the axis along the direction from the heel of the outer sole to the toe/forefoot of the outer sole.

Figure 4B:
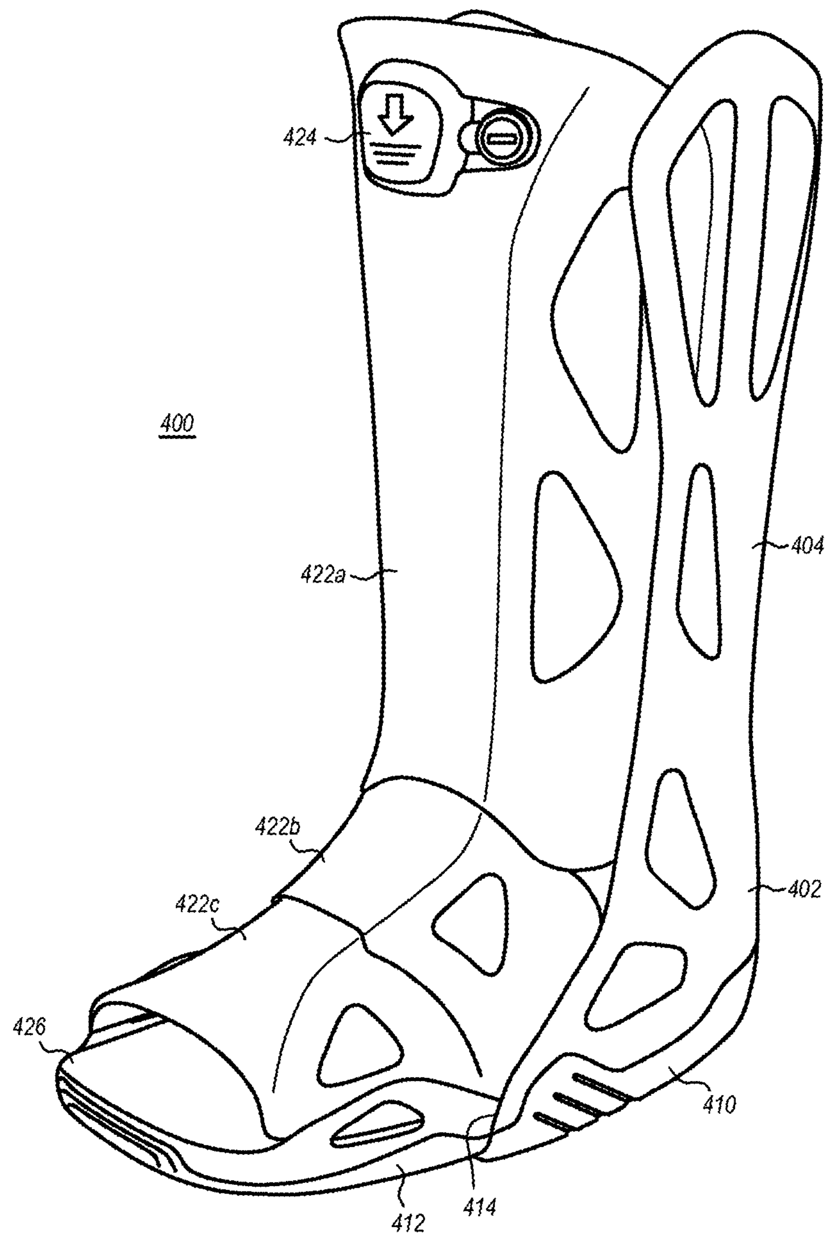

FIG. 4B shows a similar adjustable orthopedic walking boot 400 as illustrated in FIG. 4A, but with the adjustable orthopedic walking boot 400 further including anterior plates **422*a*, 422*b*, 422*c* that can be used to provide additional protection/support to the anterior portion of a user's foot and/or leg when in the walking boot 400. Although three anterior plates are depicted in FIG. 4B, it is understood that more or fewer anterior pieces can be used without departing from the scope of the present disclosure. Furthermore, although a soft component is not depicted in FIG. 4B, it is understood that a soft component with or without a pneumatic pumping system may be worn by a user and positioned between the clamshell support 404 and the anterior plates 422*a*, 422*b*, 422*c* without departing from the scope of the present disclosure. The anterior plates 422*a*, 422*b*, 422*c* can be configured such that a gap 426 can be formed proximal to the forward-most position of the forefoot portion 408 which can allow for air-flow to the user's toes and/or feet while covered with the anterior plates 422*a*, 422*b*, 422*c*. Furthermore, the walking boot 400 can include a pneumatic pumping system that includes one or more bladders (not shown) that can be filled with air or deflated upon actuation of button 424**. When filled, the bladders of the pneumatic pumping system can provide addition support to the user's leg.

A soft component (not shown) and anterior plates **422*a*, 422*b*, 422*c* may be held in position by a plurality of straps (not shown), as illustrated in FIG. 2C, that can operatively couple to the base 402 with coupling members (not shown). The straps can operatively couple to the base 402 and the clamshell support 404** using a hook-and-eye type fastener, an adhesive, a tying member, or any other type of coupling mechanism as understood by one of ordinary skill in the art.

Figure 4C:
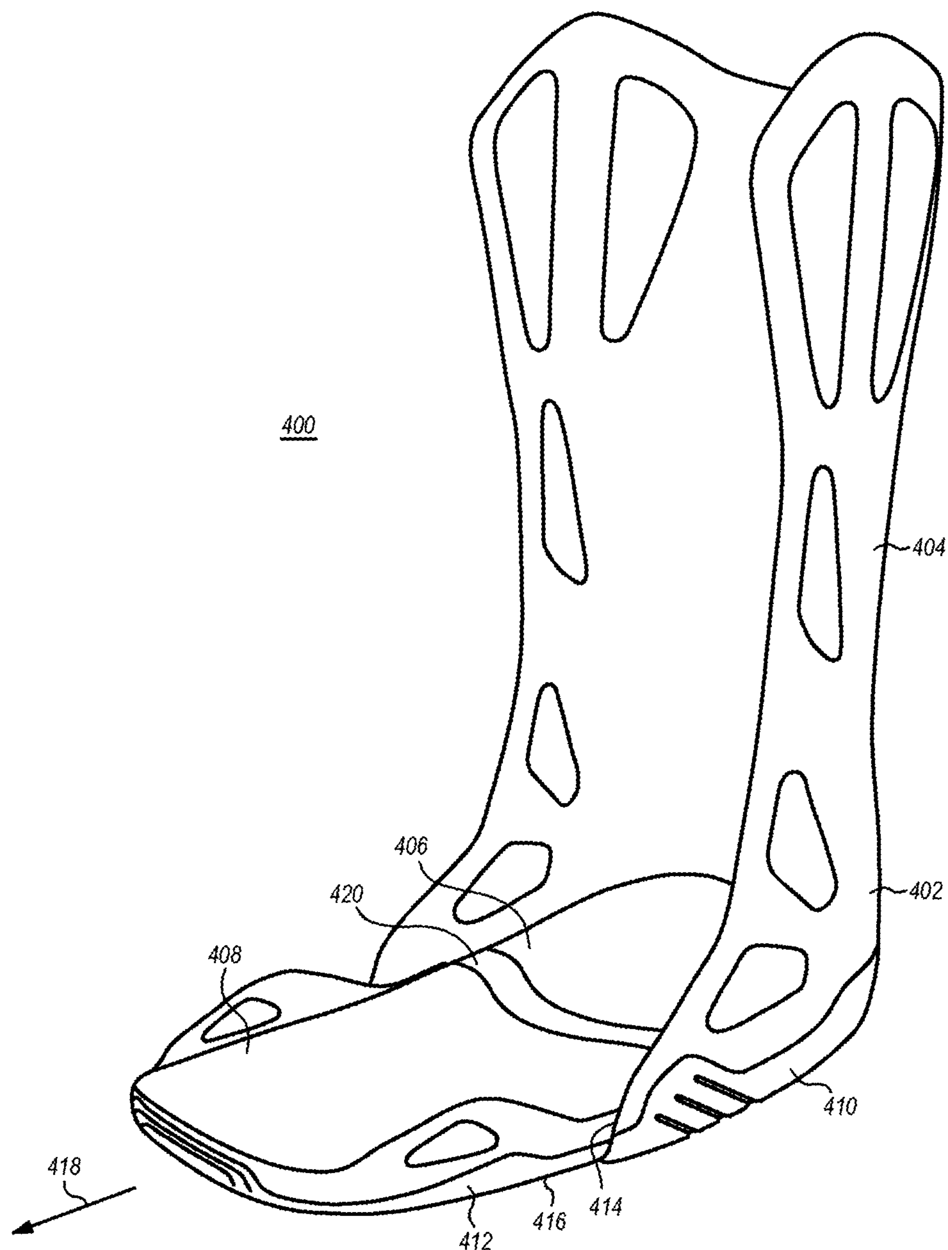

FIG. 4C illustrates the adjustable walking boot 400 of FIG. 4A but in the extended position. More specifically, the forefoot portion 408 is illustrated as being adjusted from a first position (e.g., non-extended position) to a second position (e.g., extended position) with respect to the heel portion 406. When the forefoot portion 408 is adjusted or moved from the first position to the second position, a section 416 of the second portion 412 of the outer sole moves from behind the first portion 410 of the outer sole thereby effectively extending the length of the outer sole from a first length (e.g., non-extended position) to a second length (e.g., extended position). The adjustment is illustrated by arrow 418 and can create separation gap 420 between the forefoot potion 308 and the heel portion 306 on an inner surface of the walking boot 400. Although not illustrated, the exposed section 416 may include a lip or terraced portion that is configured to mate with a forward most edge of the first portion 410 of the outer sole to provide a smooth transition between the exposed section 414 of the second portion 412 of the outer sole and the first portion 410 of the outer sole. Such a configuration can provide an even walking surface for a user, thereby increasing the stability of the walking boot 400. Conversely, when the forefoot potion 408 is adjusted from the extended position back to the non-extended position, the exposed section 416 of the second portion 412 of the outer sole retracts behind the first portion 410 of the outer sole thereby effectively shortening the length of the outer sole.

Figure 4D:
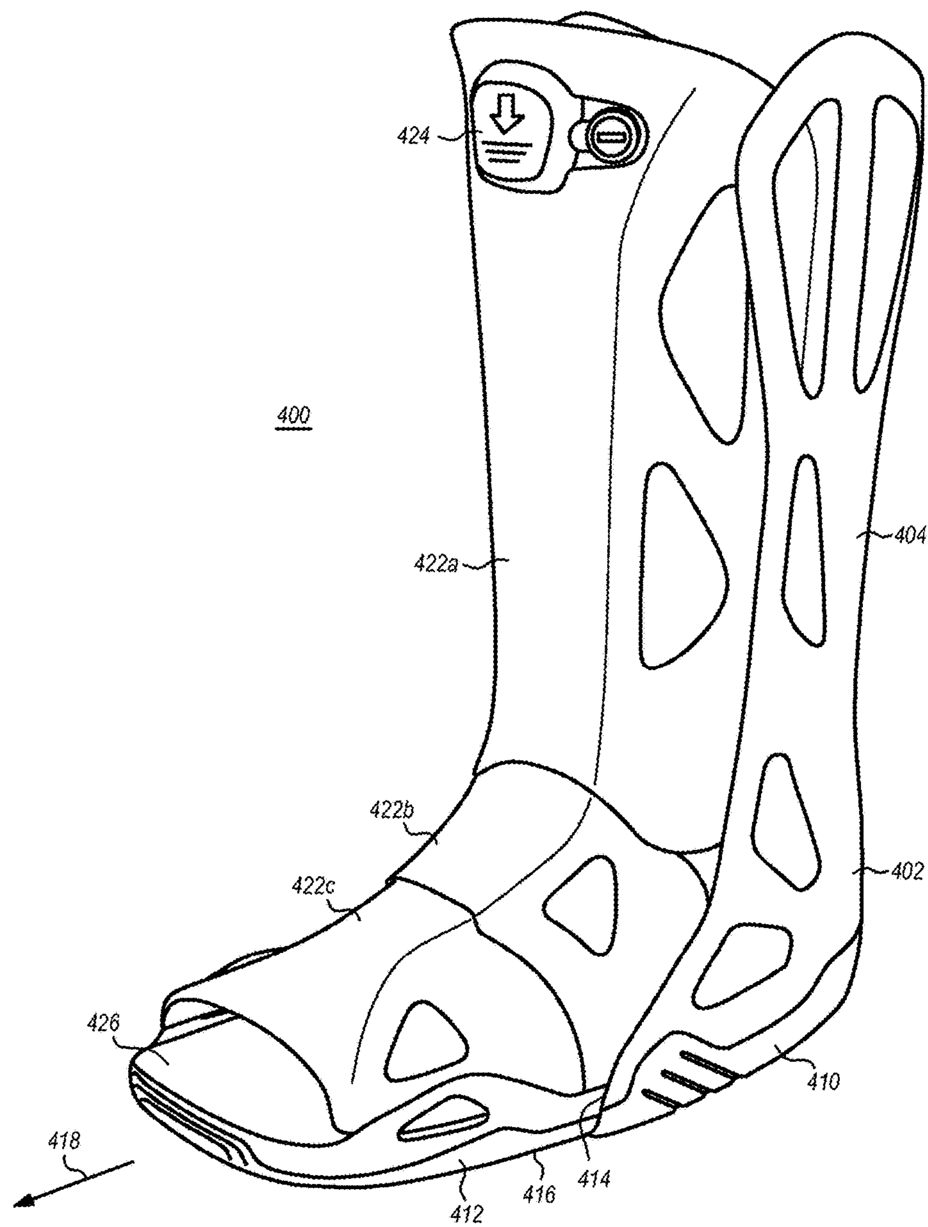

FIG. 4D illustrates the adjustable walking boot 400 with the anterior plates 422*a*, 422*b*, 422*c* depicted in FIG. 4B but with the forefoot portion 408 in the extended position as illustrated in FIG. 4C.

Figure 5A:
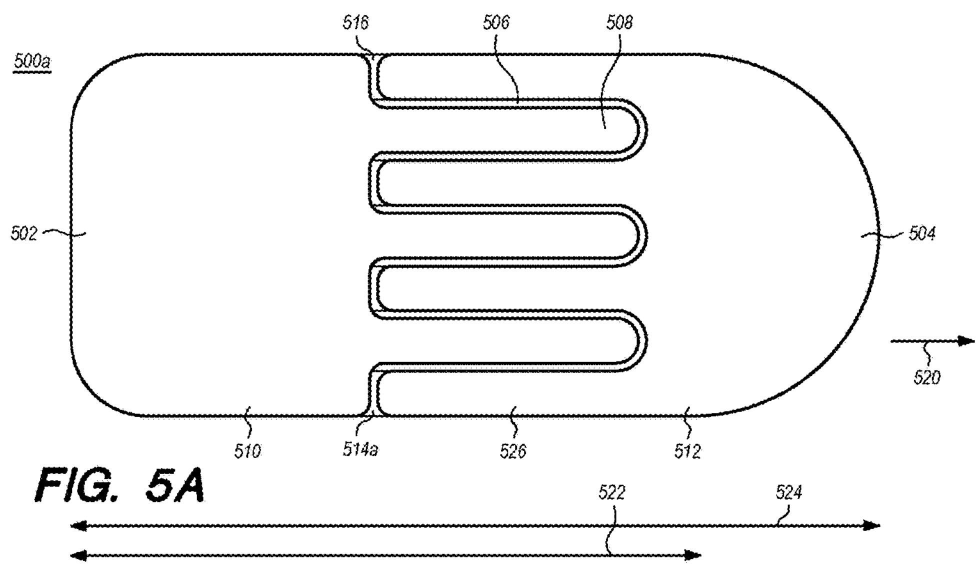
FIGS. 5A-5B illustrate a bottom perspective view of a walking apparatus in accordance with certain aspects of the present disclosure.

FIG. 5A illustrates a bottom surface view of an adjustable walking boot 500 (such as those depicted in FIGS. 3A-3B and 4A-4B where the portion of the tread/sole formed on the forefoot portion 504 form part of the walking surface of the boot when in the non-extended position) as the forefoot portion 504 is adjusted in a direction 520 to extend the length of the outer sole to accommodate a user with a larger foot size than the walking boot 500 provides when in the non-extended position. More specifically, FIG. 5A depicts one aspect in which the adjustable walking boots of the present disclosure are able to maintain a continuous tread along an entire length of the longitudinal axis of the outer sole when the adjustable walking boot is adjusted from a shorter length 522 to a larger length 524 to accommodate a larger foot size. As seen in FIG. 5A, the heel portion 502 can be formed with fingers 508 that can act as extensions of the first tread surface 510, and are configured to traverse a break 514 between the first tread surface 510 and the second tread surface 512, and completely fill in the channels 506 formed in the second tread surface 512 when the forefoot portion 504 is in the non-extended position. The forefoot portion 508 can also includes extension columns 526 of the second tread surface 512 which are formed in between the channels 506, as depicted in FIG. 5A. The extension columns 526 of the second tread surface 512 include extension sections 516 that can be positioned behind or on top of (e.g., overlap) the first tread surface 510 when the walking boot 500 is in the non-extended position. However, when the forefoot portion 504 is adjusted to the extended position, the fingers 508 of the first tread surface 510 can pull away from the channels in the second tread surface 512 forming gaps between the first tread surface 510 and the second tread surface 512. Meanwhile, the extension sections 516 of the extension columns 526 of the second tread surface 512 are exposed when the forefoot portion 504 is adjusted to the extended position which allows for a continuous tread surface along the entire length of the outer sole at least in the regions of the extension columns 526 which traverse the break 514 between the first tread surface 510 and the second tread surface 512. Having a continuous treaded surface that traverses the entire length of the outer sole when the walking boot 500 is in an extended position can provide the user with a more stable walking surface reducing the risk of slipping and injury.

According to certain aspects of the present disclosure, the extension columns 526 of the second tread surface 512 do not have to include the extension sections 516 that overlap the first tread surface 510. In such a scenario, when the forefoot portion 504 is adjusted to the extended position there may be additional gaps between the extension columns 526 and first tread surface 510 at the break 514. However, there can still be provided a substantially continuous treaded surface along the longitudinal axis of the outer sole, which can provide a stable walking surface for the user. Moreover, a predetermined radius of curvature of the outer sole of the walking boot 500 can be maintained when the forefoot portion 504 is adjusted from the non-extended position to the extended position, further details regarding the radius of curvature are provided below with respect to FIG. 5B.

Figure 5B:
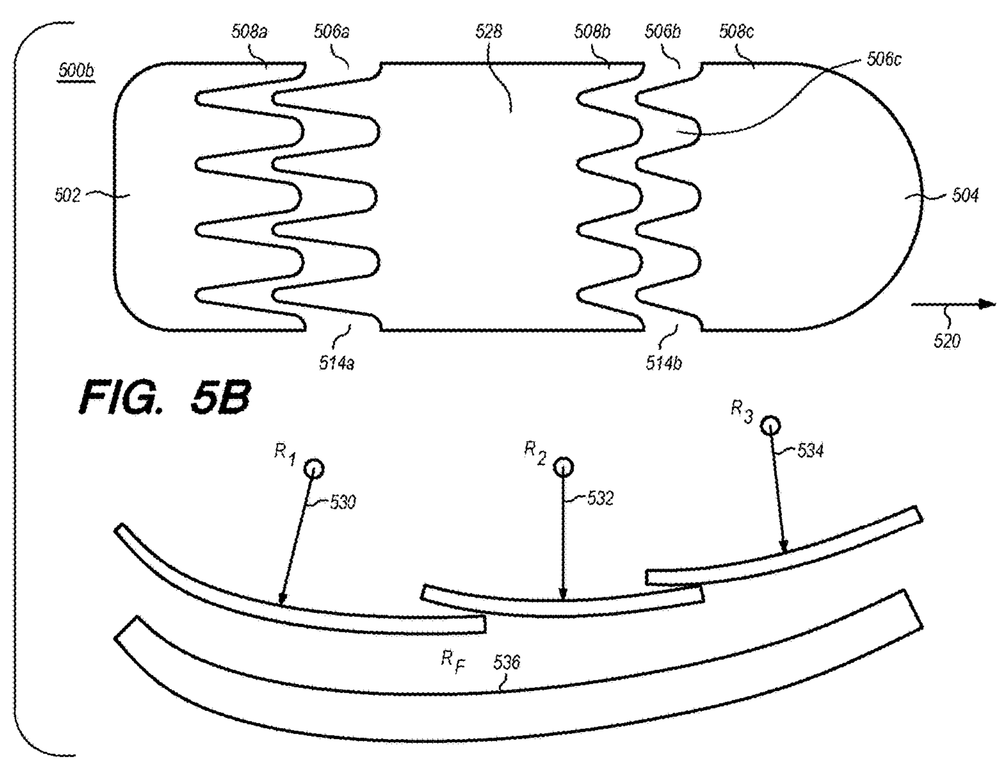

FIG. 5B illustrates a bottom surface view of an adjustable walking boot 500 (such as those depicted in FIGS. 3A-3B and 4A-4B) in which the forefoot portion 504 is adjusted in a direction 520 to extend the length of the outer sole to accommodate a user with a larger foot size. More specifically, FIG. 5B depicts manners in which the adjustable walking boots of the present disclosure are able to maintain a fixed radius of curvature $R_f$ when the length of adjustable walking boot is adjusted from a shorter length to a larger length.

FIG. 5B is depicted as including a midfoot portion 528 that is adjustable with respect to the heel portion 502 and/or the forefoot portion 504. Each of the heel portion 502, the midfoot portion 528, and the forefoot portion 504 include respective channels 506*a*, 506*b*, 506*c* and fingers 508*a*, 508*b*, 508*c* which are similarly structured as those detailed above with respect to FIG. 5A. In addition, the fingers 508*a*, 508*b*, 508*c* can act as extension column including (or not) including extension sections (illustrated in FIG. 5A) that overlap adjacent tread surface on one or more of the heel portion 502, the midfoot portion 528, and/or the forefoot portion 508*c*, and which traverse one or more of the breaks 514*b* located therebetween.

As illustrated in FIG. 5B, each of the heel portion 502, the midfoot portion 528, and the forefoot portion 504 is configured with a respective radius of curvature $R_1$, $R_2$, and $R_3$ that when combined provide the outer sole with an overall radius of curvature $R_f$. Each of the heel portion 502, the midfoot portion 528, and the forefoot portion 504 can be configured such that regardless of being in the non-extended position or one or more extended positions the overall radius of curvature is substantially maintained at $R_f$. Having a non-zero $R_f$ for the overall outer sole can provide the user with a curved bottom boot that can enable easier mobility for the user.

Figure 6A:
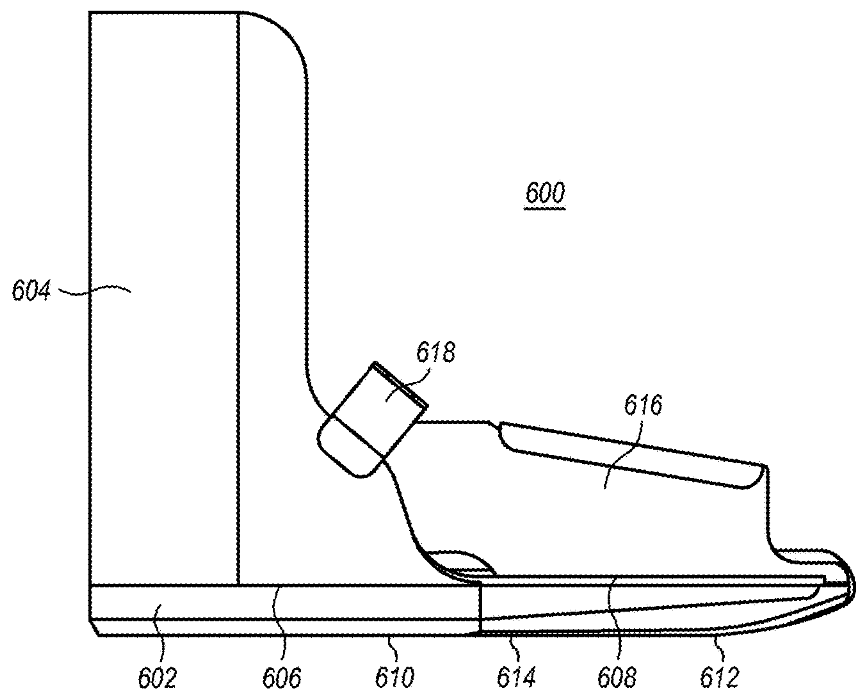
FIGS. 6A-6B illustrate a side view of a walking apparatus in accordance with certain aspects of the present disclosure.
Figure 6B:
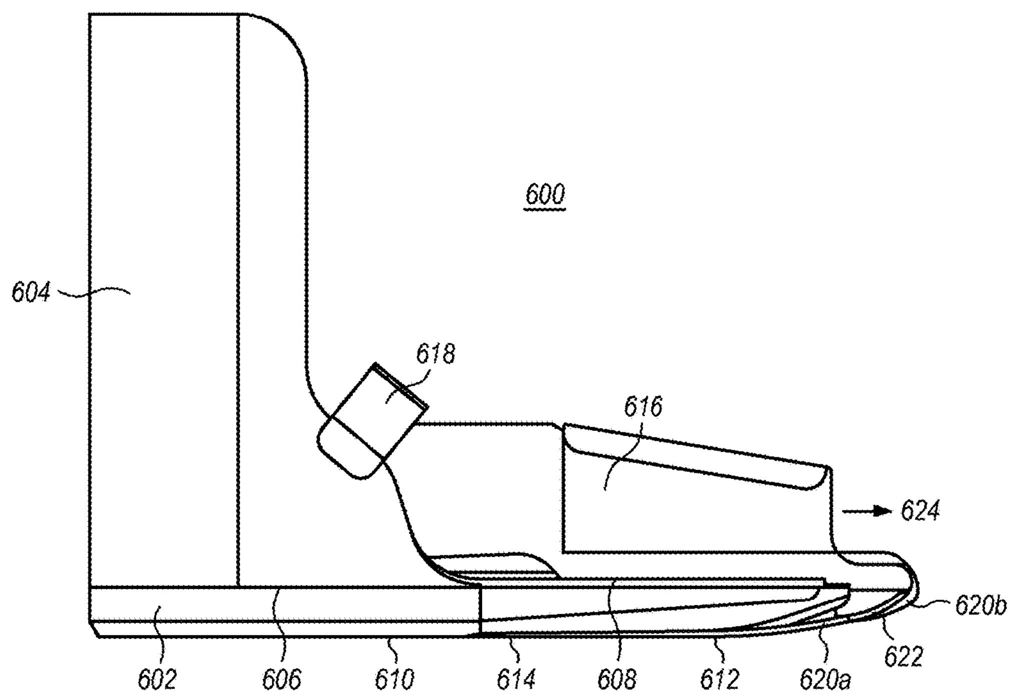

FIGS. 6A and 6B illustrate an adjustable orthopedic and/or post-operative walking shoe 600, according to one aspect of the present disclosure, that can include a rigid, semi-rigid, or soft back support 604, a rigid, semi-rigid, or soft dorsal forefoot support 616 (e.g., made of a breathable material and including attachment straps couplable to one another), and/or ankle support strap 618. FIG. 6A shows the adjustable walking shoe 600 in a non-extended configuration. The outer sole can completely cover the bottom surface of the base 602 and be made up of a first section 610 and a second section 612. In particular, the first section 610 of the outer sole can cover the heel portion 606 of the base 602, while the second section 612 of the outer sole can cover the forefoot portion 608 of the base 602. As seen in the FIG. 6A, the entire second section 612 of the outer sole does not remain behind the first section 610 of the outer sole when the forefoot portion 608 is in a non-extended position with respect to the heel portion 606, as depicted in FIG. 1A. Instead, in the non-extended position, a break 614 in the outer sole proximal to a midsection of the base 602 can allow the first section 610 and at least a portion of the second section 612 of the outer sole to form the walking surface of the walking boot 600. Although the break 614 is illustrated as being near a midsection of the base 602, it is understood that the break 614 can be positioned anywhere along the longitudinal axis of the base 602 without departing from the scope of the present disclosure. Moreover, the outer sole may extend up the sides of the perimeter of the walker base 602 to maximize surface contact between the outer sole and the base 602, in a similar manner described with respect to FIG. 3A.

FIG. 6B illustrates the adjustable walking boot 600 depicted FIG. 6A but in the extended position. More specifically, the forefoot portion 608 is illustrated as being adjusted from a first position (e.g., non-extended position) to a second position (e.g., extended position) with respect to the heel portion 606. When the forefoot portion 608 is adjusted or moved from the first position to the second position, sections 620*a*, 620*b* of the second portion 612 of the outer sole extend from behind the second portion 612 of the outer sole thereby effectively extending the length of the outer sole from a first length (e.g., non-extended position) to a second length (e.g., extended position) providing a smooth interface between the second portion 612 of the outer sole and the extension sections 620*a*, 620*b*. As seen in FIG. 6B, toe section 620*b* can be coupled to extension section 620*a* with member 622 that is contained within toe section 620*b*. Alternately, toe section 620*b* can be coupled to the extension section 620*b* using an adhesive, a screw, a snap fit configuration, and any other coupling mechanism as understood by one of ordinary skill in the art. Still further, toe section 620*b* and extension section 620*a* can be formed as a unitary structure without departing from the scope of the present disclosure. Although not illustrated, the exposed section 620*a* may include a lip or terraced portion that is configured to mate with a forward most edge of the second portion 612 of the outer sole to provide a smooth transition between the exposed section 620*a* of the second portion 612 of the outer sole and the second portion 612 of the outer sole. Such a configuration can provide an even walking surface for a user, thereby increasing the stability of the walking boot 600. Conversely, when the forefoot potion 68 is adjusted from the extended position back to the non-extended position, the exposed section 620*a* and the toe portion 620*b* of the second portion 612 of the outer sole retracts at least partially behind the second portion 612 of the outer sole thereby effectively shortening the length of the outer sole.

Figure 7A:
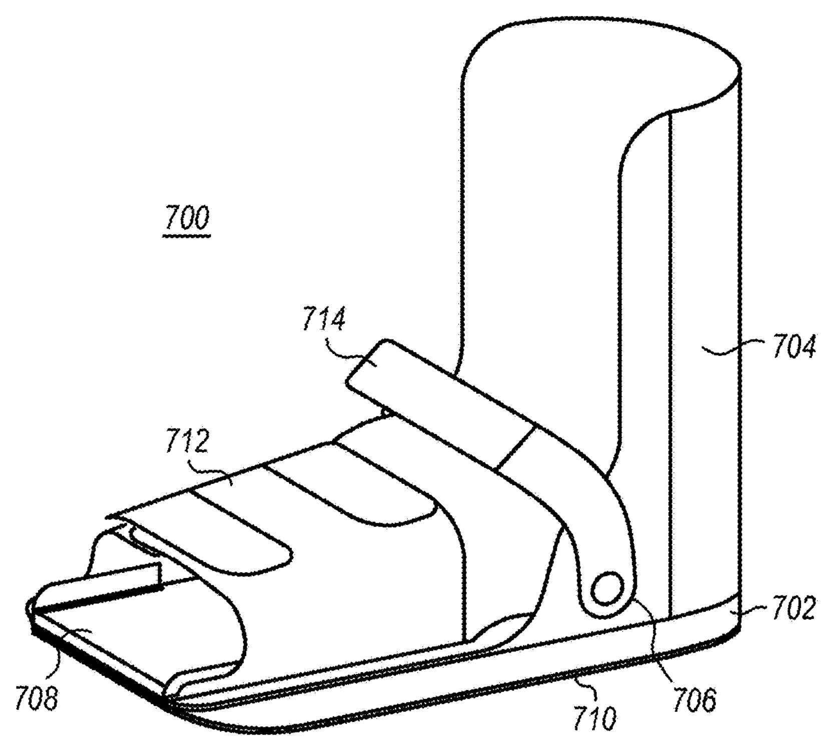
FIGS. 7A-7E illustrate a side view of a walking apparatus in accordance with certain aspects of the present disclosure.
Figure 7B:
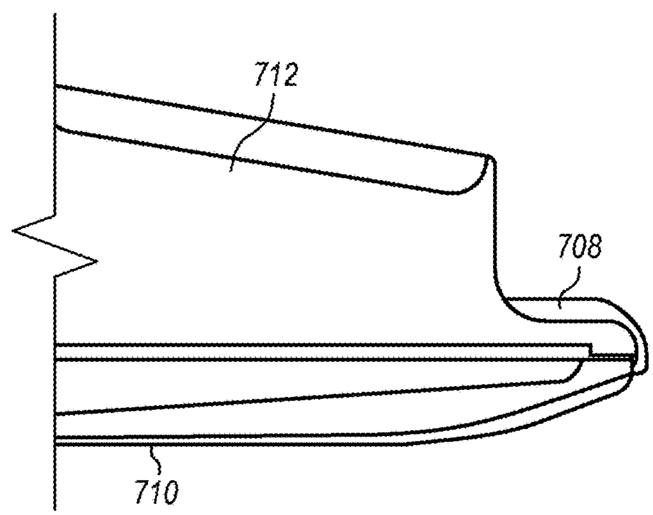

FIGS. 7A-7E illustrate an adjustable orthopedic and/or post-operative soft walking shoe 700 that can include a rigid, semi-rigid, or soft back support 704 (e.g., made of a breathable material and including attachment straps couplable to one another), a rigid, semi-rigid, or soft dorsal forefoot support 712 (e.g., made of a breathable material and including attachment straps couplable to one another), and/or ankle support strap 714. FIG. 7A shows the adjustable walking shoe 700 in a non-extended configuration. The outer sole can completely cover the bottom surface of the base 702 and be made up of a unitary first section 710 when the walking shoe 700 is in the non-extended position. In particular, the unitary first section 710 of the outer sole can cover the heel portion 706 of the base 702 and the forefoot portion 708 of the base 702 when in the non-extended position. In addition, the outer sole may extend up the sides of the perimeter of the walker base 702 to maximize surface contact between the outer sole and the base 702, in a similar manner described with respect to FIG. 3A. FIG. 7B shows a side profile of the soft walking boot 700 illustrated in FIG. 7A in the non-extended position.

Figure 7C:
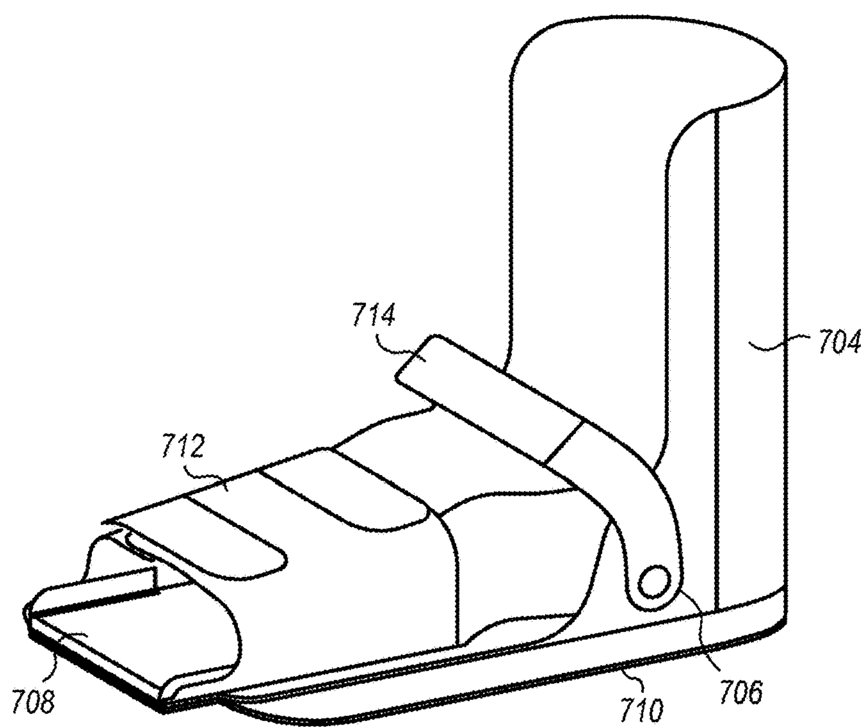
Figure 7D:
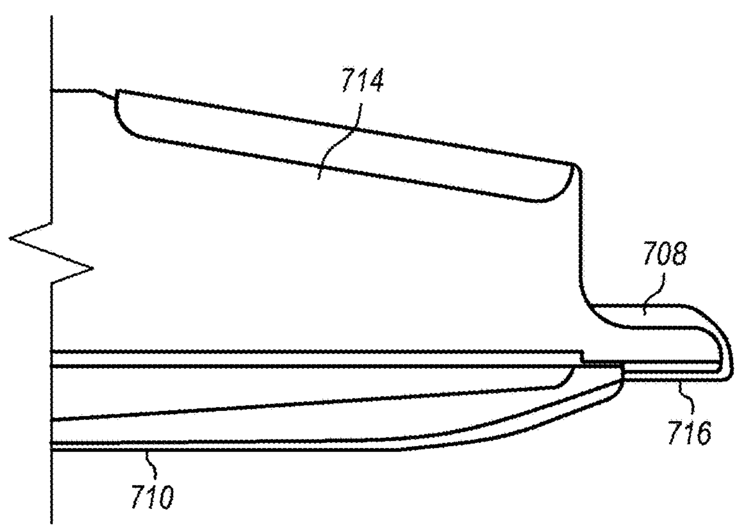
Figure 7E:
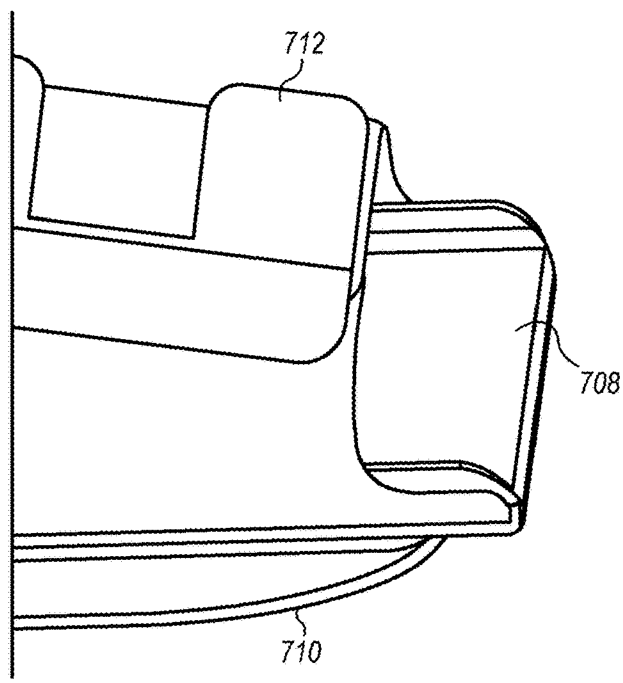

FIG. 7C illustrates the adjustable walking boot 700 depicted in FIG. 7A but in the extended position. More specifically, the forefoot portion 708 is illustrated as being extended from a first position (e.g., non-extended position) to a second position (e.g., extended position) with respect to the heel portion 706. When the forefoot portion 708 is adjusted or moved from the first position to the second position, the forefoot portion 708 extends out of the dorsal forefoot support 712 and past a forward-most edge of the unitary first section 710. The forefoot portion 708 extending past the forward-most edge of the unitary first section 710 can include a second section (not shown) of the outer sole that provides an extended walking surface when the forefoot portion 708 extends past the unitary first section 710. FIGS. 7D-7E show a side profile and a top angled view of the soft walking boot 700 illustrated in FIG. 7C in the extended position.

Figure 8A:
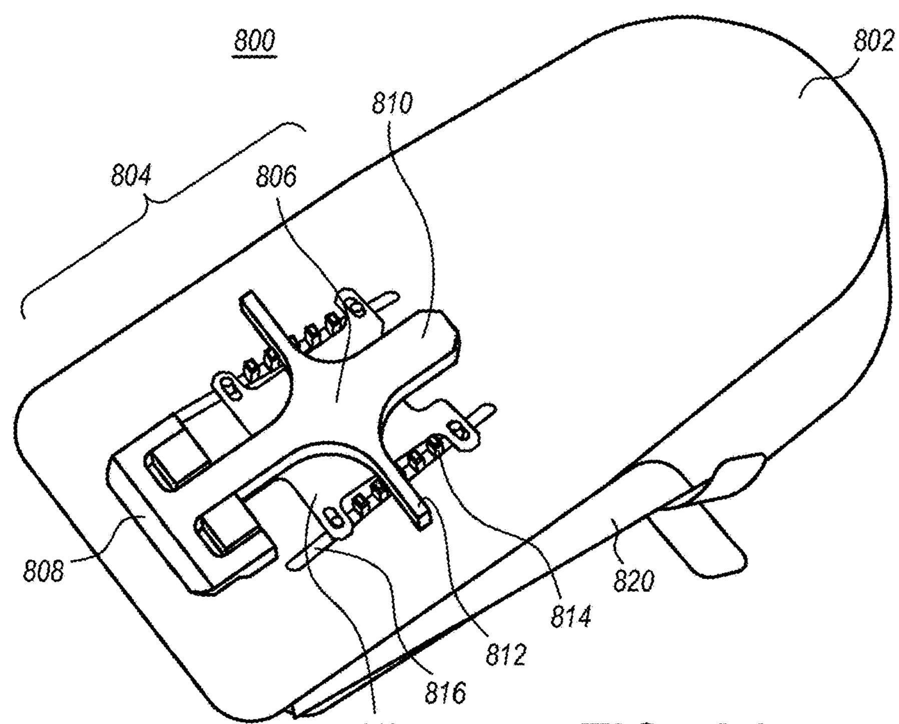
FIGS. 8A-8B illustrate an actuation mechanism of a walking apparatus in accordance with certain aspects of the present disclosure.
Figure 8B:
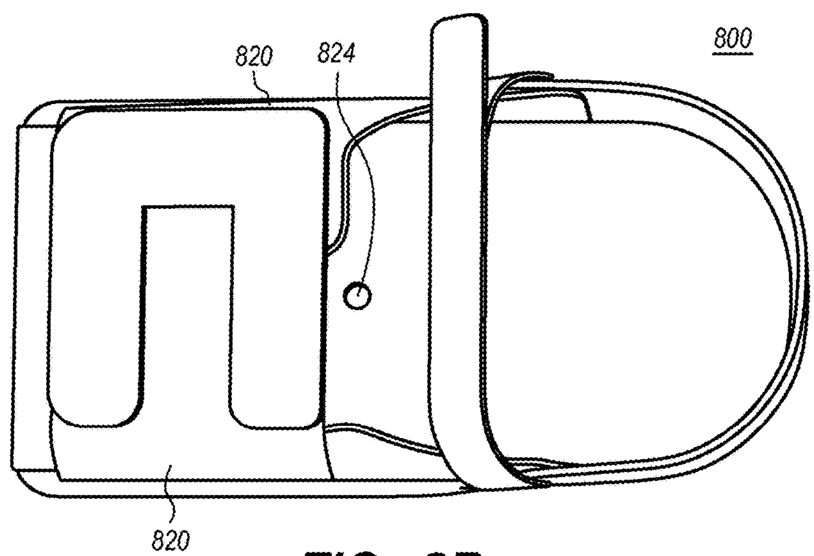

FIGS. 8A and 8B illustrate two different views of a post operative shoe including an actuation mechanism that can be configured to facilitate the adjustment of the forefoot portion from the non-extend position, in accordance with one aspect of the present disclosure. Although the actuation mechanism is depicted as being included in a post-operative shoe 800, it is understood that the actuation mechanism detailed below with respect to FIGS. 8A and 8B can be included in any number of different types of walking apparatus such as those illustrated in all the other figures included in the present disclosure. For example, the types of walking apparatuses that can include the actuation member illustrated in FIG. 8A can include an open-toe orthopedic walking boot, a closed-toe orthopedic walking boot, an orthopedic walking boot including bilateral struts, an orthopedic walking boot including a clamshell configuration, a soft component of an orthopedic walking boot, a post-operative shoe, a clinical walker, and a hospital walker, just to name a few.

As seen in FIG. 8A, the actuation mechanism 804 can be operatively coupled to the base 802 of a walking apparatus 800. The actuation mechanism can include a cantilever member 806 that is made up of a spring loaded end 808 that is at least partially fixed to a portion of the underside of the base 802 and an unfixed end 810 that can be configured to pivot when an actuation force is applied thereto. As further illustrated in FIG. 8A, a pair of arms 810 can be operatively coupled at a predetermined angle to the cantilever member 806. When an actuation force of a sufficient amount is applied to the unfixed end 810 of the cantilever member 806, the pair of arms 812 can clear the height of ridges 814, which allows the base plate 818 and the cantilever member to move freely along tracks 816. This movement of the base plate 818 can be configured to enable the adjustment of the forefoot portion of the base from a first position to a second different position thereby extending or shortening the length of the walking apparatus 800. Once the forefoot portion has been adjusted to a desired position, the actuation force can be removed from the unfixed end 810 of the cantilever member 806, which can allow the pair of arms 812 to relax back down between ridges 814. This can disenable movement of the forefoot portion until another actuation force is applied to the cantilever member.

As further illustrated in FIG. 8A, the base plate 818 can be operatively coupled to dorsal toe portions 820 and configured to enable an adjustment of the dorsal toe portions and the forefoot portion at the same time. By way of example, the tracks 816 can be formed at an angle with respect to one another which can enable a widening or a narrowing of the dorsal toe portions 820 as the forefoot portion is adjusted from the first position to the second position. FIG. 8B is a top view of the adjustable walking apparatus 800 which illustrates an aperture 824 in the inner sole, which allows access to the unfixed end 810 of the cantilever 806 so that an actuation force can be applied thereto to adjust the length of the walking apparatus 800.

Figure 9A:
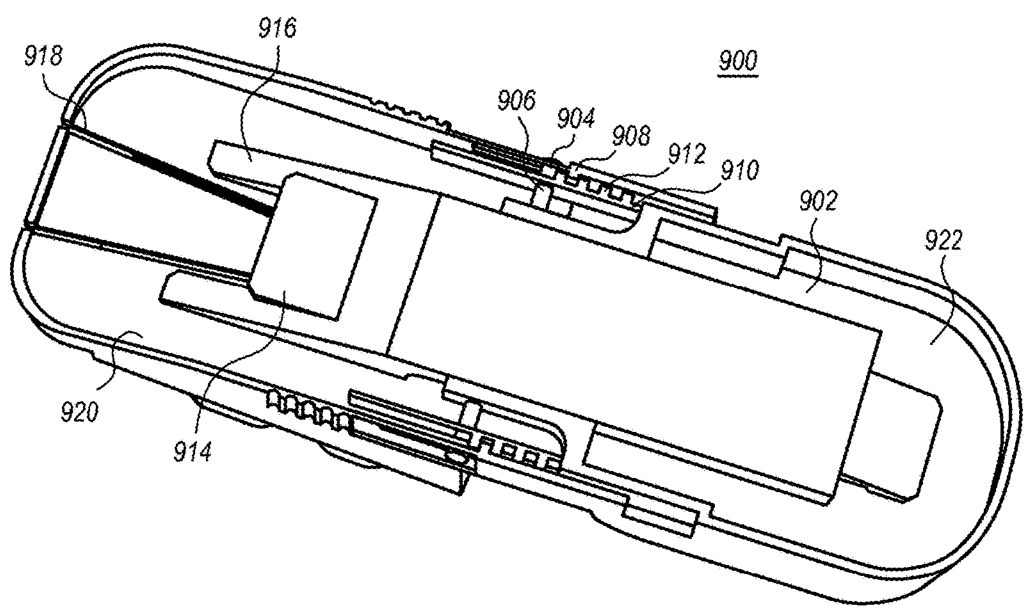
FIGS. 9A-9B illustrate an actuation mechanism of a walking apparatus in accordance with certain aspects of the present disclosure.
Figure 9B:
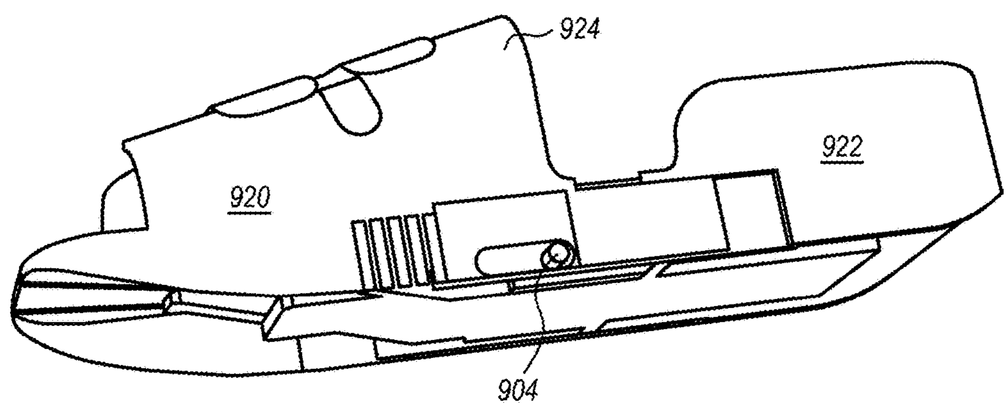

FIGS. 9A and 9B illustrate two different views of a post operative shoe 900 including an actuation mechanism that can be configured to facilitate the adjustment of the forefoot portion from the non-extend position, in accordance with one aspect of the present disclosure. Although the actuation mechanism is depicted as being included in a post-operative shoe 900, it is understood that the actuation mechanism detailed below with respect to FIGS. 9A and 9B can be included in any number of different types of walking apparatus such as those illustrated in all the other figures included in the present disclosure. For example, the types of walking apparatuses that can include the actuation member illustrated in FIG. 9A can include an open-toe orthopedic walking boot, a closed-toe orthopedic walking boot, an orthopedic walking boot including bilateral struts, an orthopedic walking boot including a clamshell configuration, a soft component of an orthopedic walking boot, a post-operative shoe, a clinical walker, and a hospital walker, just to name a few.

As seen in FIG. 9A, the actuation mechanism can be operatively coupled to the base 902 of a walking apparatus 900. The actuation mechanism can include an actuator button 904 operatively coupled to a spring 906 and a boss member 908 operatively coupled to the forefoot portion 920 of the base 902 that is configured to engage with ridges 912 operatively coupled to the heel portion 922 of the base 902. The ridges 912 are in an opposing configuration with respect to the boss member 908 and engage the boss member 908 such that the forefoot portion 920 is held in a fixed position with respect to the heel portion 922. However, when a force of a predetermined amount is applied to the actuator button 904, the preloaded spring 906 decompresses which can cause an upward movement of the spring 904 that forces the boss 908 out of engagement from the ridges 912, thereby enabling movement of the forefoot portion 920 with respect to the heel portion 922. The forefoot portion 920 can be operatively coupled to tracks 918 using a male slide member 914 and a female slide member 916. This movement can result in an extension of the length of the walking apparatus 900.

FIG. 9B is a side view of the adjustable walking apparatus 900 which illustrates the actuator button 904 positioned on a side portion of the walking apparatus. As appreciated by one of ordinary skill in the art, the actuator button can be positioned anywhere on the walking apparatus 900 that enables ease of use and comfort for the user. In addition, there may be a single actuator button 904 or a plurality of actuator buttons that can be actuated simultaneously or individually without departing from the scope of the present disclosure.

As illustrated in FIG. 9B, a dorsal toe portion 924 is depicted as being integrally formed with the forefoot portion 920 and which moves with the forefoot portion 920 when the actuator button 904 is actuated. However, as also understood, the dorsal toe portion 924 can include separate components operatively coupled to the male slide 914 and the female slide 916 such that the dorsal toe portions 924 can also move along with the forefoot portion 920 when they are not integrally formed therewith.

Furthermore, the tracks 918 can be formed at an angle with respect to one another which can enable a widening or a narrowing of the dorsal toe portions as the forefoot portion 920 is adjusted from the first position to the second position.

Figure 10A:
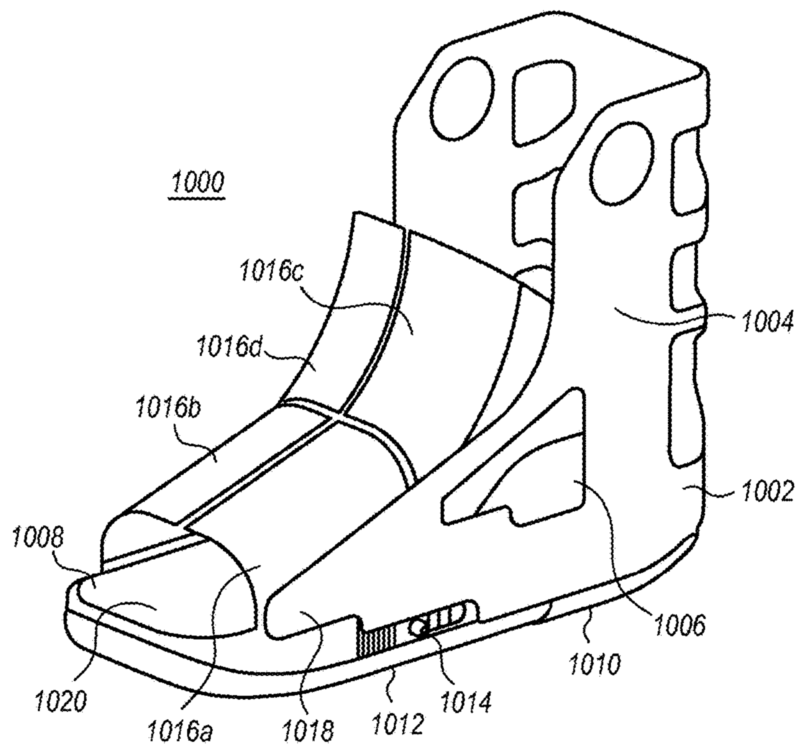
FIGS. 10A-10B illustrate a side view of a walking apparatus in accordance with certain aspects of the present disclosure.
Figure 10B:
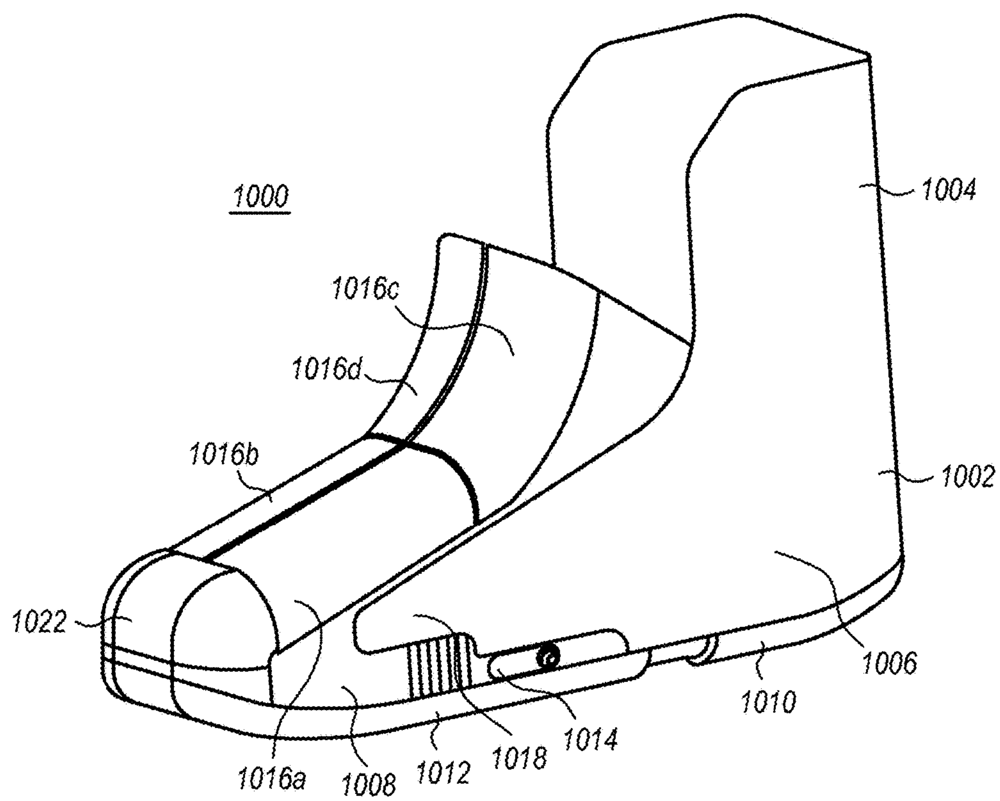

FIGS. 10A and 10B illustrate adjustable walking boots configured for lengthwise and widthwise adjustment. More specifically, FIG. 10A depicts an adjustable walking boot 1000 including a clamshell support structure 1004 operatively coupled to a base 1002. The base 1002 can include a heel portion 1006 and a forefoot portion 1008. An outer sole of the walking boot 1000 can be made up of a first section 1010 which covers the heel portion 1006 of the base 1002, and a second section 1012 that covers the forefoot portion 1008 of the base 1002. The walking boot 1000 illustrated in FIG. 10A can further include dorsal forefoot components 1016*a*, 1016*b*, 1016*c*, 1016*d* that are configured to protect the foot and ankle of a user. A tapered side portion 1018 that is operatively coupled to the heel portion is configured to engage with the dorsal forefoot components 1016*a*, 1016*b*, 1016*c*, 1016*d* and hold them in a fixed position when the forefoot portion 1008 is in a fixed position relative to the heel portion 1006. The dorsal forefoot components 1016*a*, 1016*b*, 1016*c*, 1016*d* can provide a gap 1020 in the toe portion of the walking boot 1000 to allow air flow into the boot. An actuation mechanism 1014 similar to that illustrated in FIGS. 9A and 9B can be included in the base 1002, which can enable the adjustment of the forefoot portion 1008 and the dorsal forefoot components 1016*a*, 1016*b*, 1016*c*, 1016*d* from a first position to a second position with respect to the heel portion 1006. The geometry of the tapered side portion 1018 is configured to enable an adjustment in the width of the dorsal forefoot components 1016*a*, 1016*b*, 1016*c*, 1016*d* when the forefoot portion is moved from a first position to a second position by enabling an expansion or compression of the dorsal forefoot components 1016*a*, 1016*b*, 1016*c*, 1016*d*, as the components move past or retract into contact with the outer contact point of the tapered side portion 1018.

FIG. 10B is directed to a similar adjustable walking boot 1000 as depicted in FIG. 10A, except that the dorsal forefoot components 1016*a*, 1016*b*, 1016*c*, 1016*d* further include toe closure component 1022 that provides additional protection to the toe region of the user's foot.

Figure 11A:
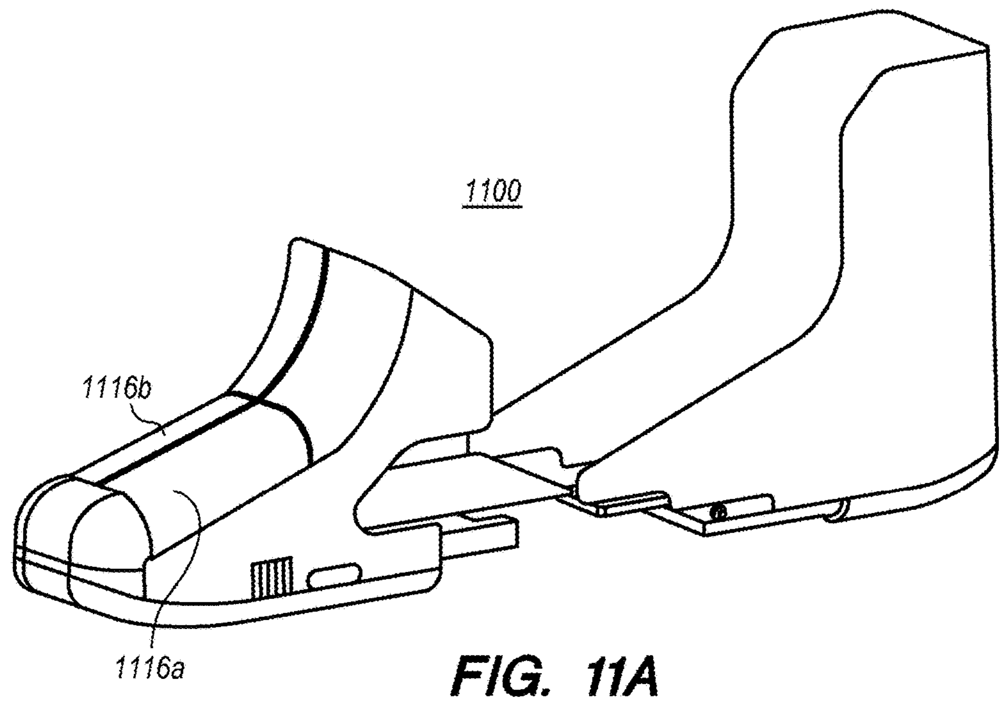
FIGS. 11A-11B illustrate a side view of a walking apparatus in accordance with certain aspects of the present disclosure.
Figure 11B:
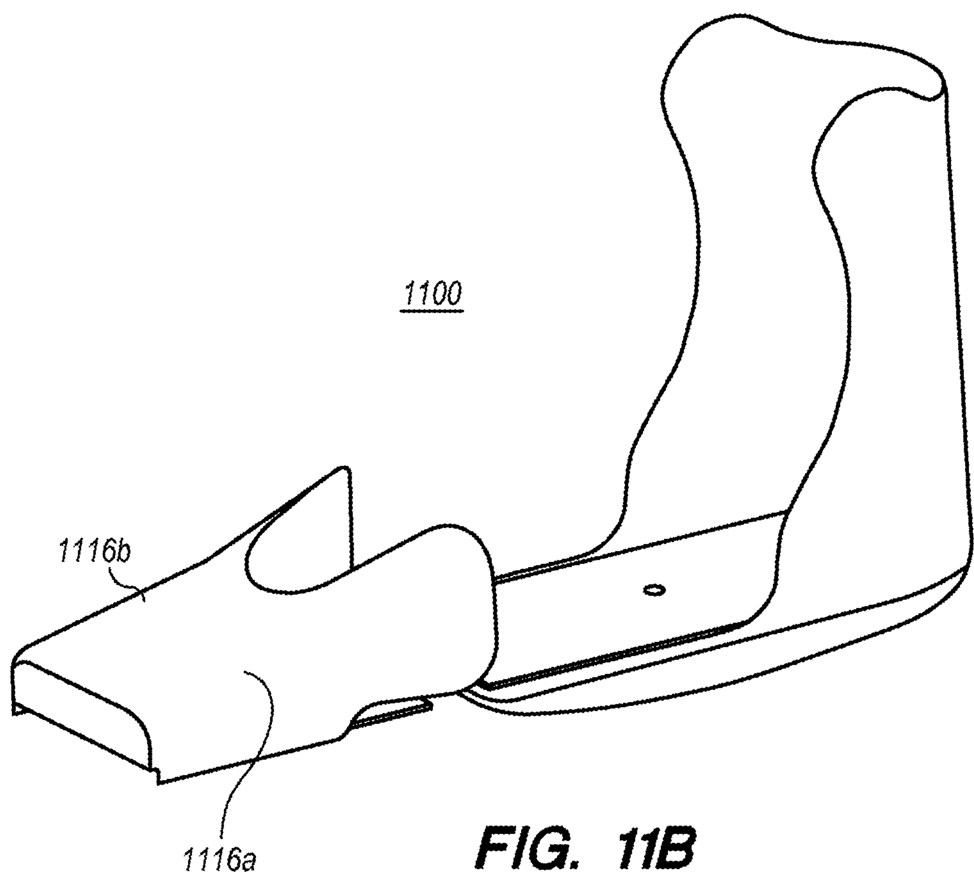

FIGS. 11A and 11B depict an adjustable walking boot 1100 including dorsal forefoot components and a toe closure component similar to those described with respect to FIGS. 10A and 10B. However, adjustable walking boot 1100 illustrated in FIGS. 11A and 11B is enable a widening or narrowing of the dorsal forefoot components 1116*a*, 1116*b* using a split-toe configuration. The dorsal forefoot components 1116*a*, 1116*b* can be configured to remain in a fixed position when the forefoot portion is fixed relative to the heel portion without requiring the tapered side portion 1018 illustrated in FIGS. 10A and 10B.

Figure 12:
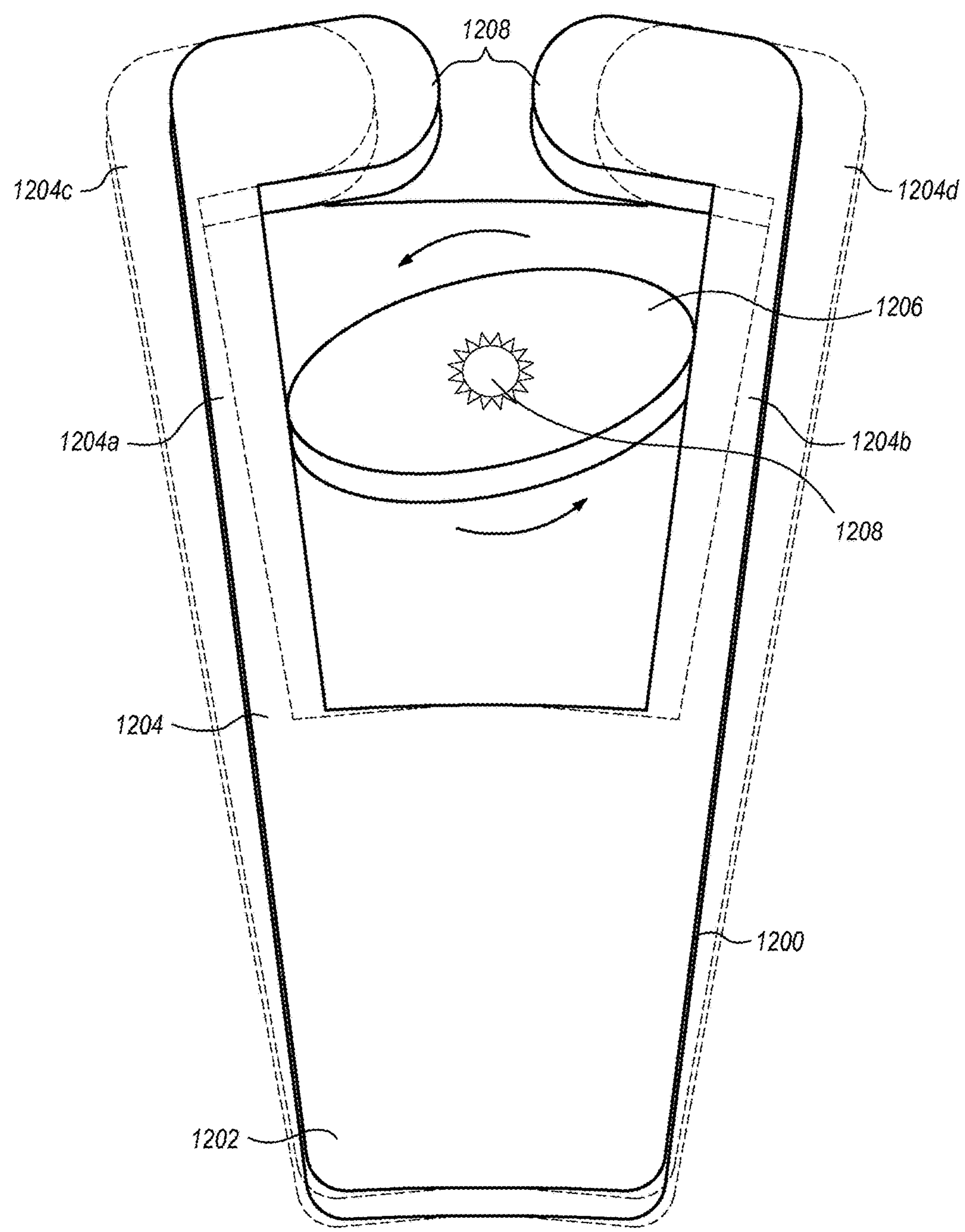
FIG. 12 illustrates a top view of a base portion of a walking apparatus in accordance with certain aspects of the present disclosure.

FIG. 12 illustrates one aspect of the present disclosure in which a forefoot portion 1204 of a base 1200 of a walking apparatus includes a left forefoot portion 1204*a* and a right forefoot portion 1204*b* that include an overlapping region 1208 proximal to the toe of the walking apparatus. A cam 1206 accessible from the inner sole or side portion of the base, for example, is configured to adjust a width of the forefoot portion 1204 when actuated. For example, the cam 1206 can include an aperture 1208 that is configured to receive a tool that enables a rotation of the cam 1206. The cam 1206 is shaped such that when rotated, the left forefoot portion 1204*a* and the right forefoot portion 1204*b* are adjusted to respective expanded positions 1204*c* and 1204*d*. Conversely, the cam 1206 can be actuated to narrow the width of the toe in a similar manner described above. Moreover, the width of the walking apparatus can be adjusted independently of the length of the walking apparatus according to certain aspects of the present disclosure.

Figure 13A:
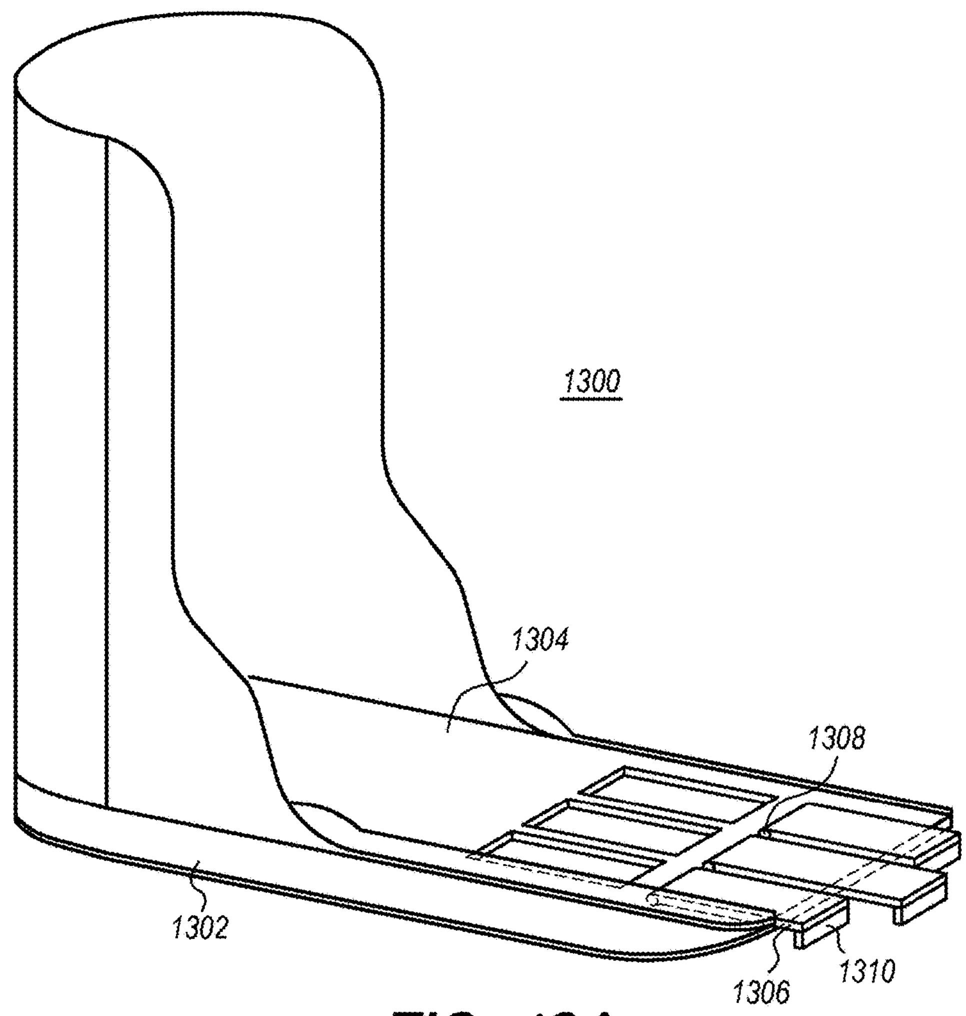
FIGS. 13A-13B illustrate a side view of a walking apparatus in accordance with certain aspects of the present disclosure.
Figure 13B:
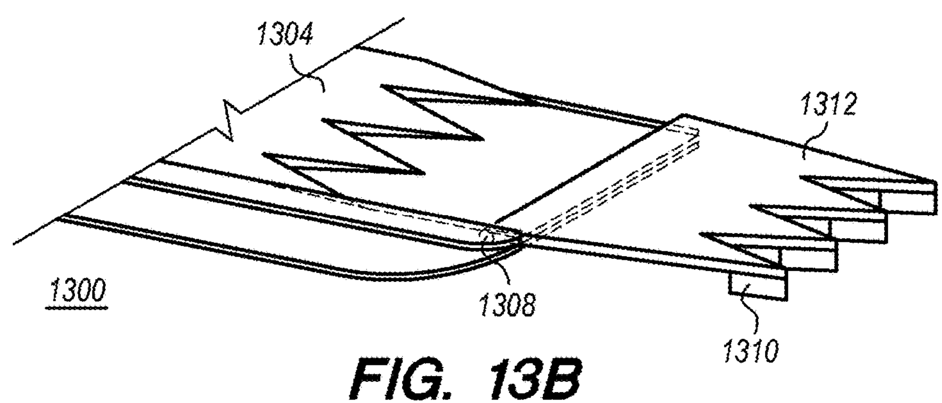

FIGS. 13A and 13B illustrate adjustable walking boots 1300 in accordance with certain aspects of the disclosure. More specifically, FIG. 13A depicts an adjustable walking boot 1300 that includes multiple extension members 1306 that are each attached to the inner sole 1304 of the walking boot with a hinge member 1308. When the length of the walking boot needs to be adjusted, the extension portions 1306 can be folded out to provide the required extra length. Although not shown, a locking mechanism can be used to ensure that the extension portions 1306 are locked into place once they are folded out. Furthermore, each of the extension members 1306 can be configured with a tread or pad 1310 to provide a stable surface on which the user can safely use as a walking surface. FIG. 13B depicts an adjustable walking boot 1300 that includes a single extension member 1312 attached with a hinge 1308 to the inner sole 1304 of the boot. The single extension member 1312 can be locked into position and configured with a single or multiple treads or pads 1310 to provide a stable surface on which the user can use as a walking surface. Although three rectangular extension members 1306 are illustrated in FIG. 13A and a single fold out member with a tooth-like edge is illustrate in FIG. 13B, the fold out extension member(s) 1306 can take on any geometry, size, or quantity without departing from the scope of the present disclosure.

Figure 14:
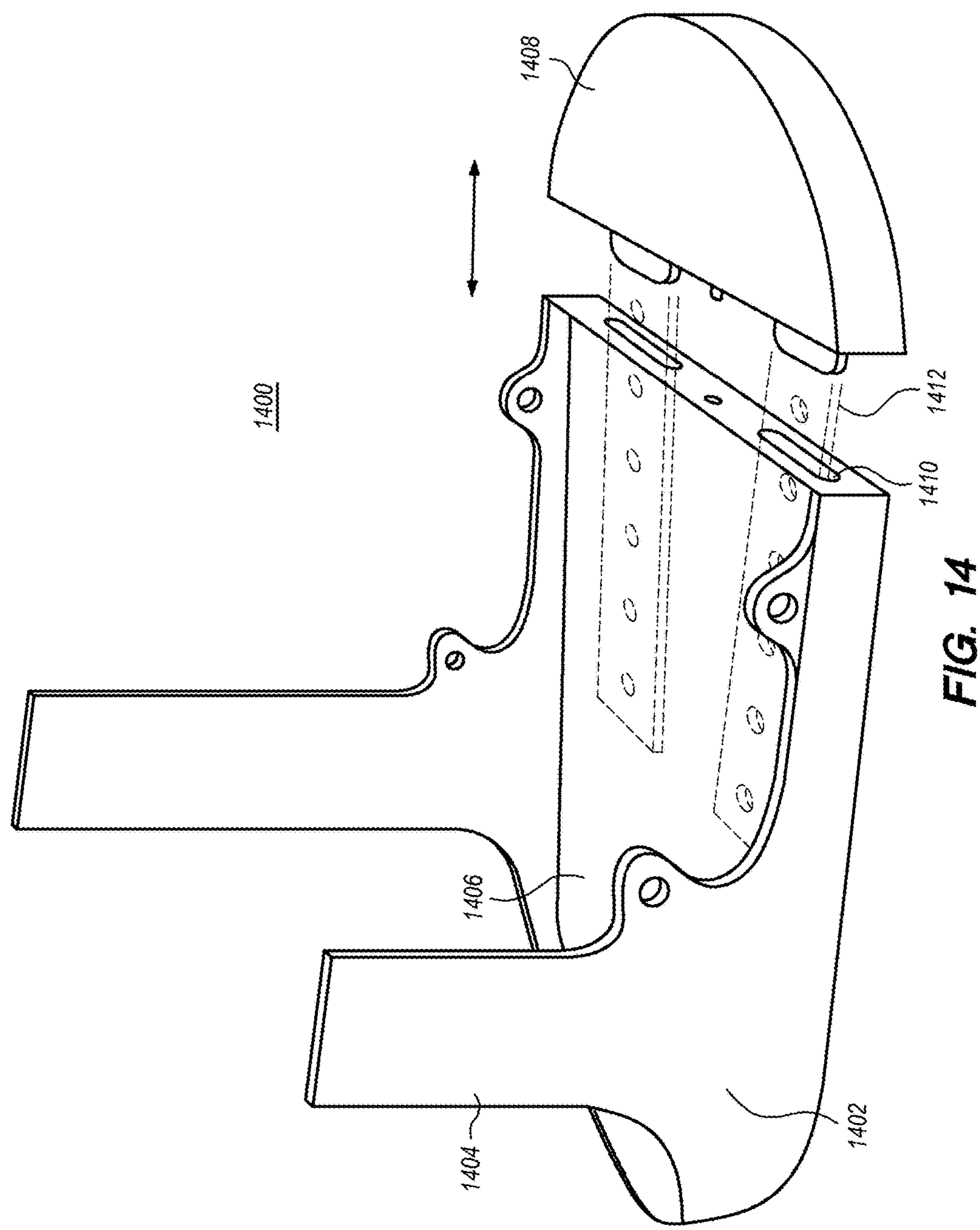
FIG. 14 illustrates a side view of a walking apparatus in accordance with certain aspects of the present disclosure.

FIG. 14 depicts an assembly kit configured to provide an adjustable walking boot 1400 when assembled. The assembly kit includes a base 1402 that can be made up of a support structure 1404 (e.g., bilateral struts or a clamshell configuration) and a heel portion 1406. The base 1402 includes one or more channels 1410 configured to receive extension portion(s) 1412 of the forefoot component 1408 of the assembly kit. The extension portions 1412 can include any geometry and/or size and are configured to provide stability and support along a longitudinal axis of the assembled walking boot 1400. The assembly kit can include multiple forefoot components 1408 each of a different length to accommodate a variety of foot sizes.

Figure 15:
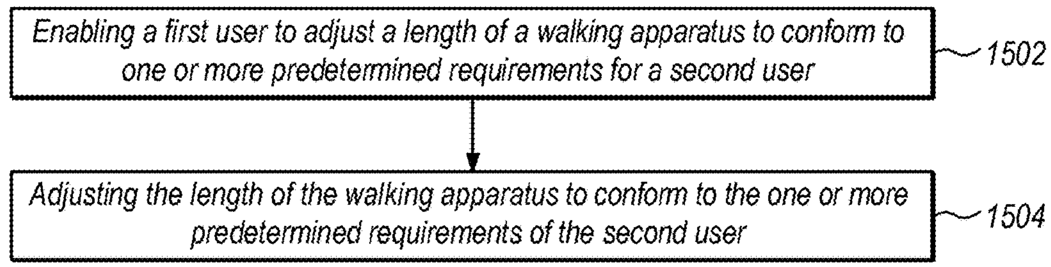
FIG. 15 illustrates a method of adjusting a characteristic of a walking apparatus in accordance with certain aspects of the present disclosure.
Figure 16A:
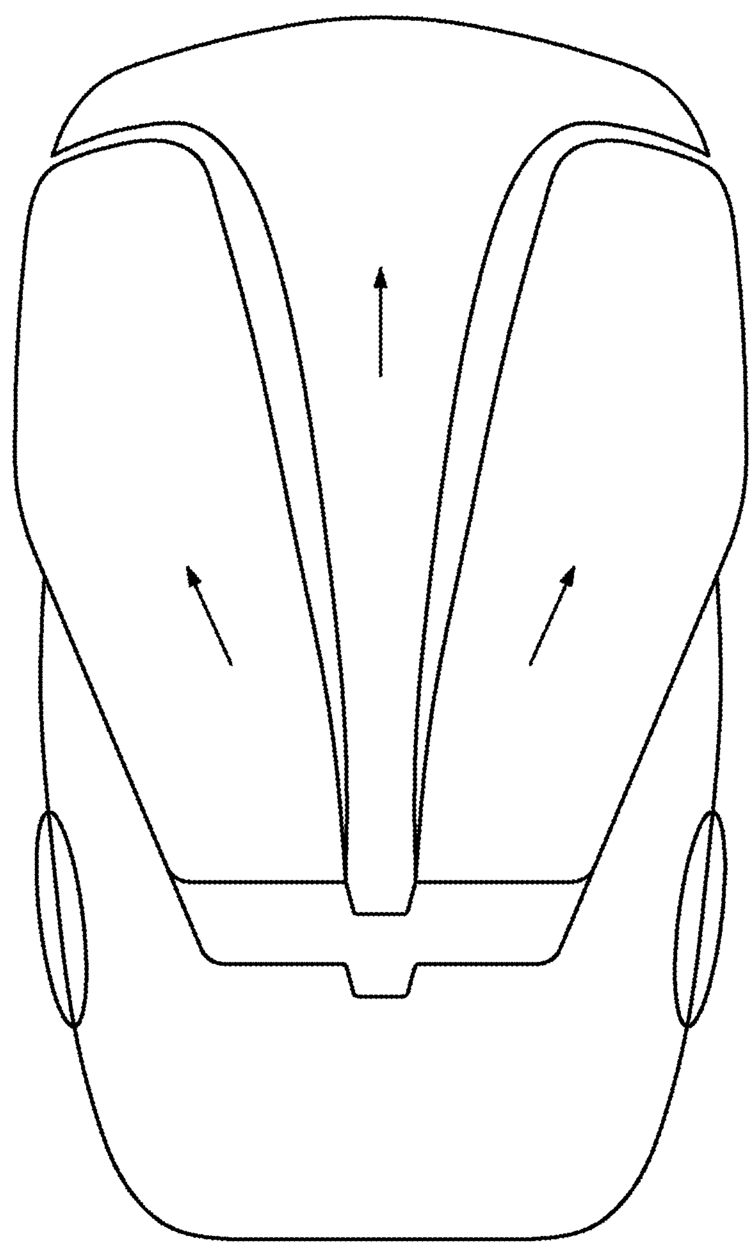
FIGS. 16A-16G illustrate various views of a walking apparatus in accordance with certain aspects of the present disclosure.
Figure 16B:
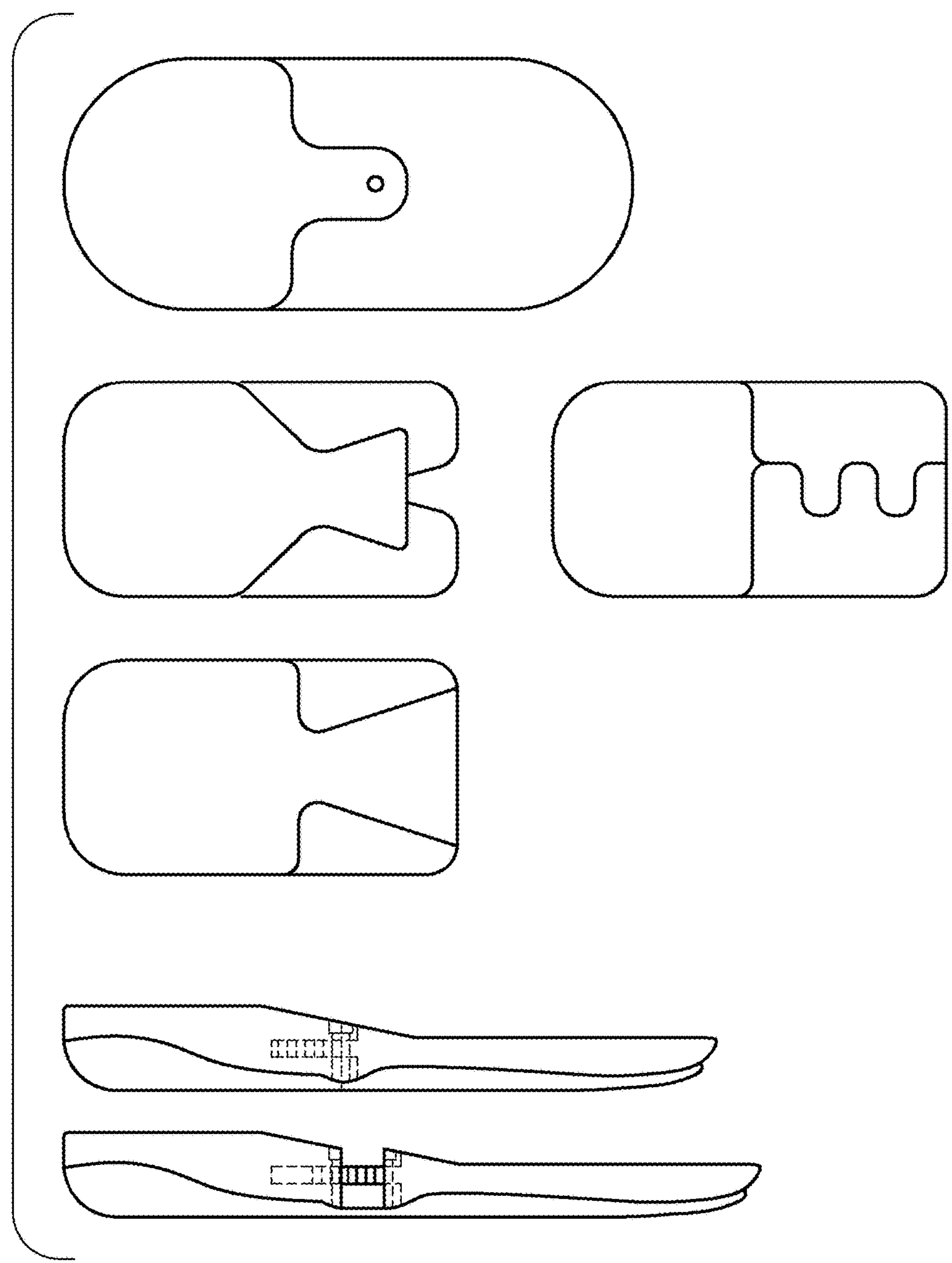
Figure 16C:
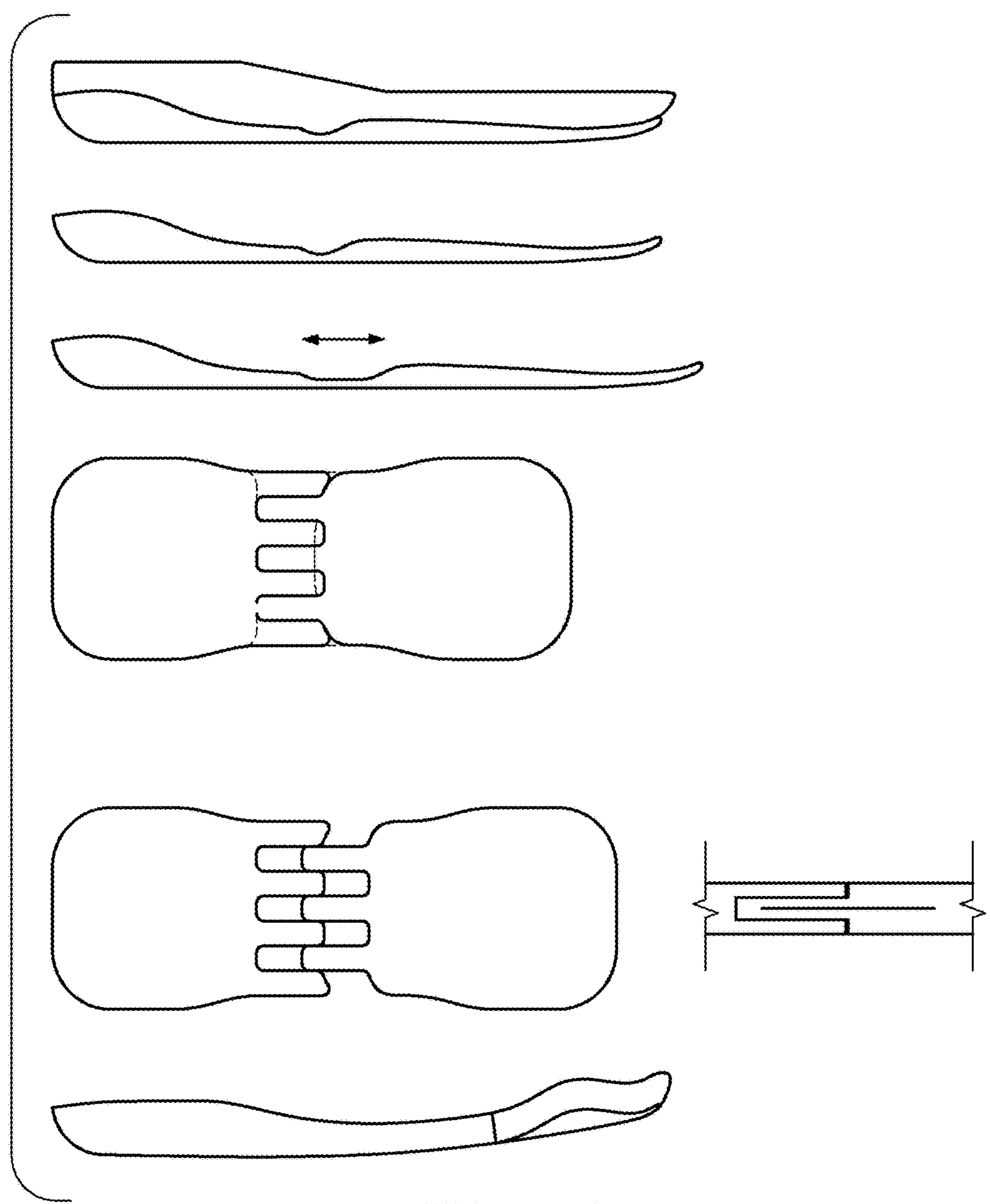
Figure 16D:
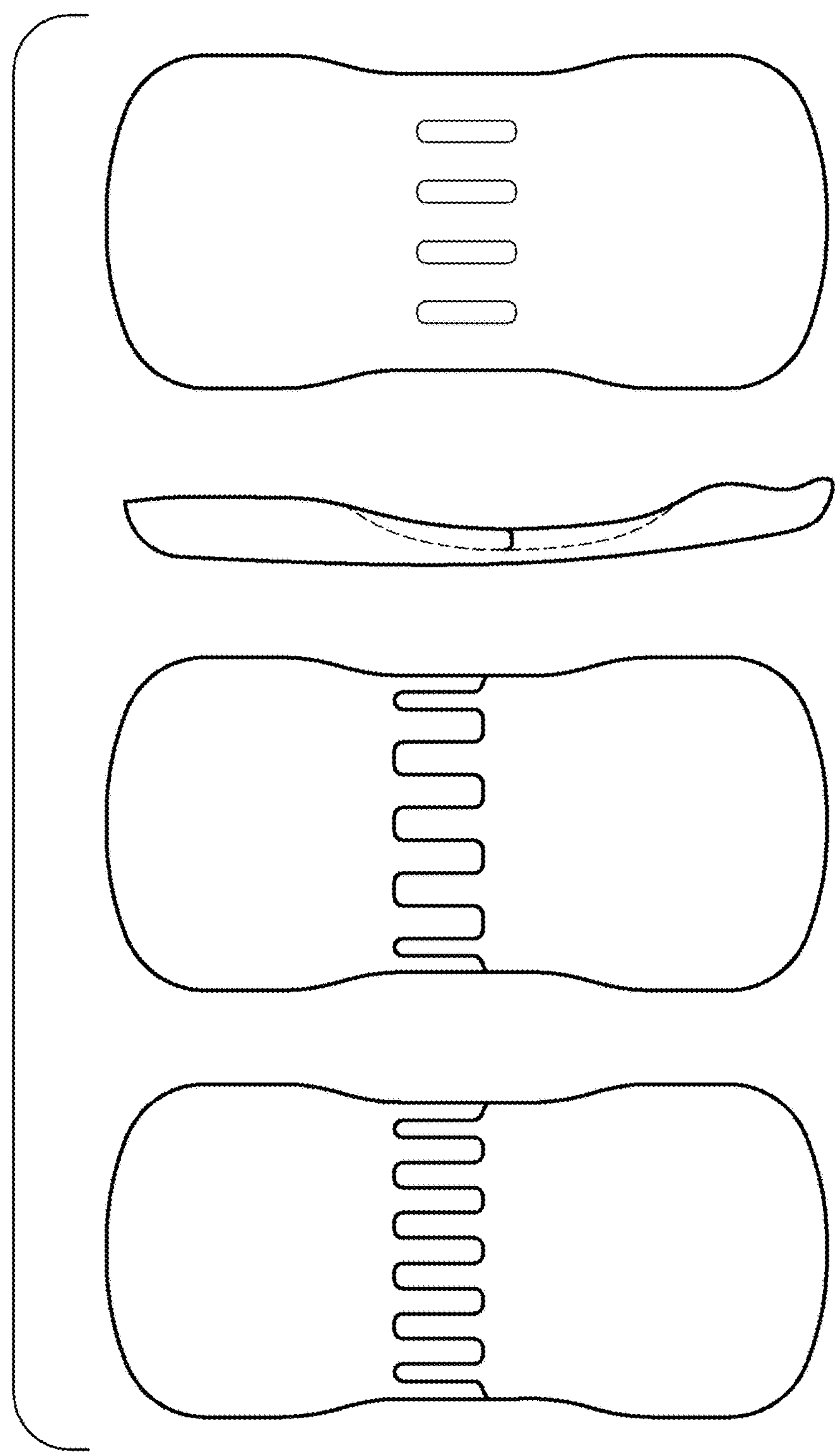
Figure 16E:
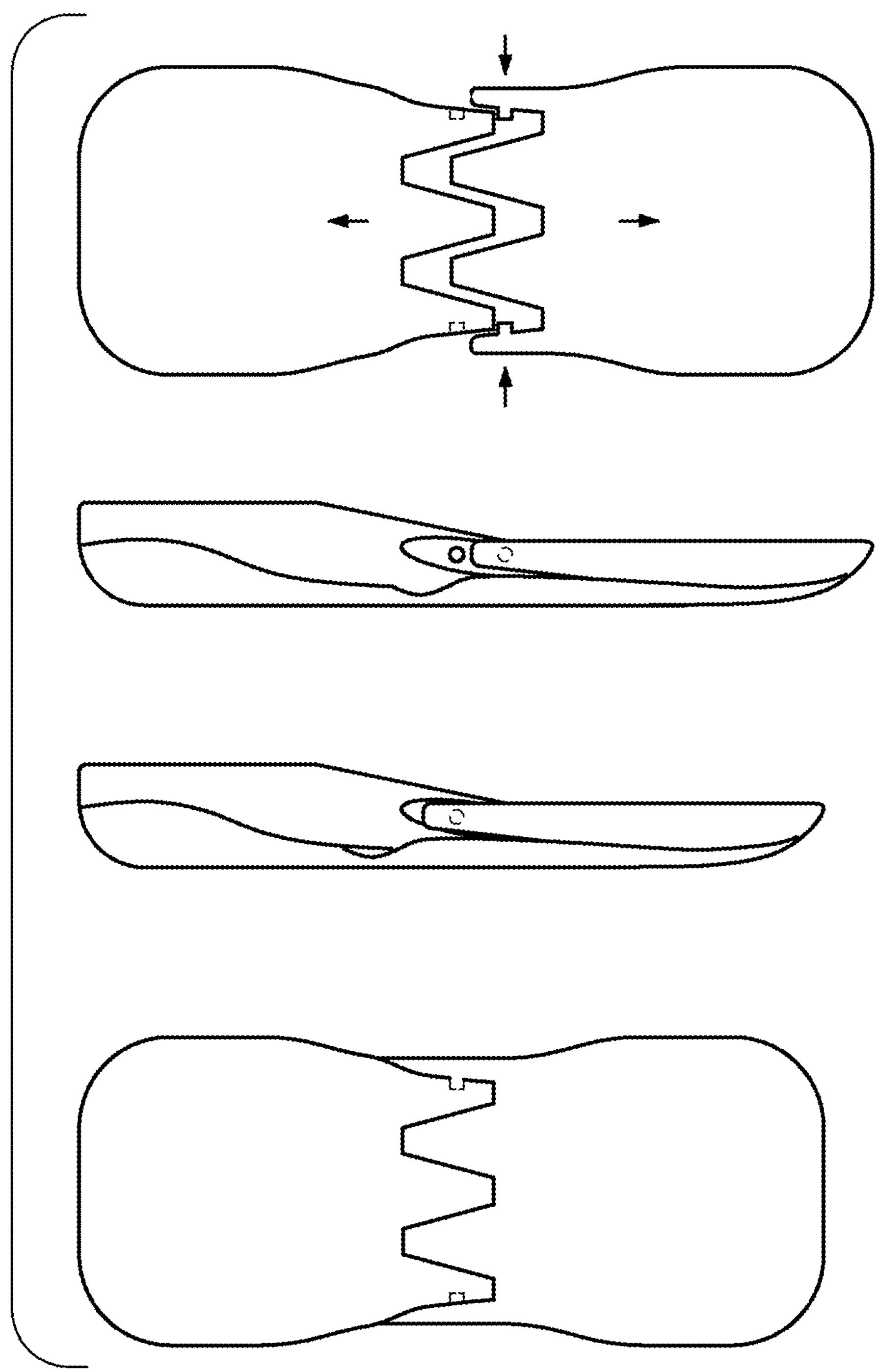
Figure 16F:
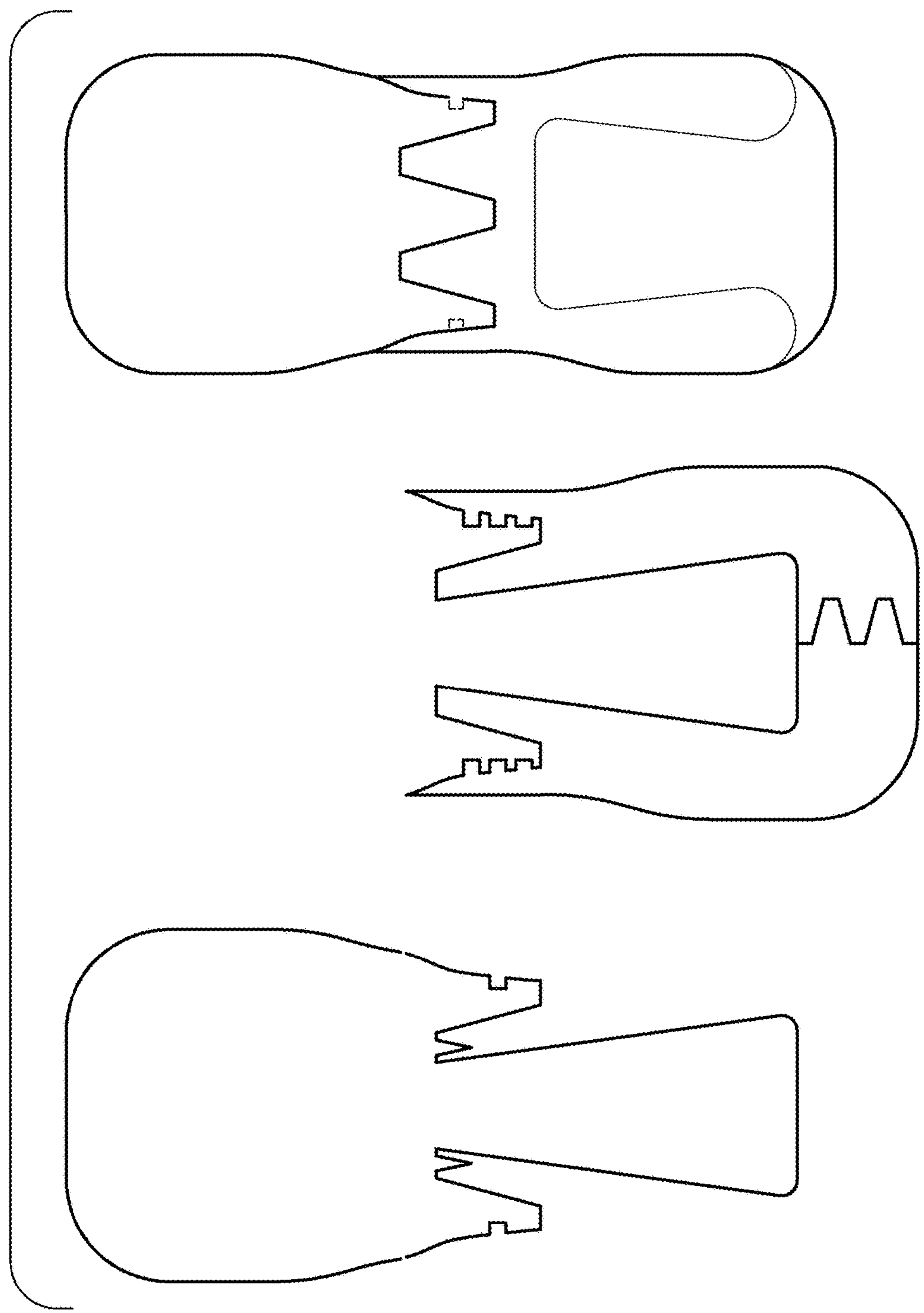
Figure 16G:
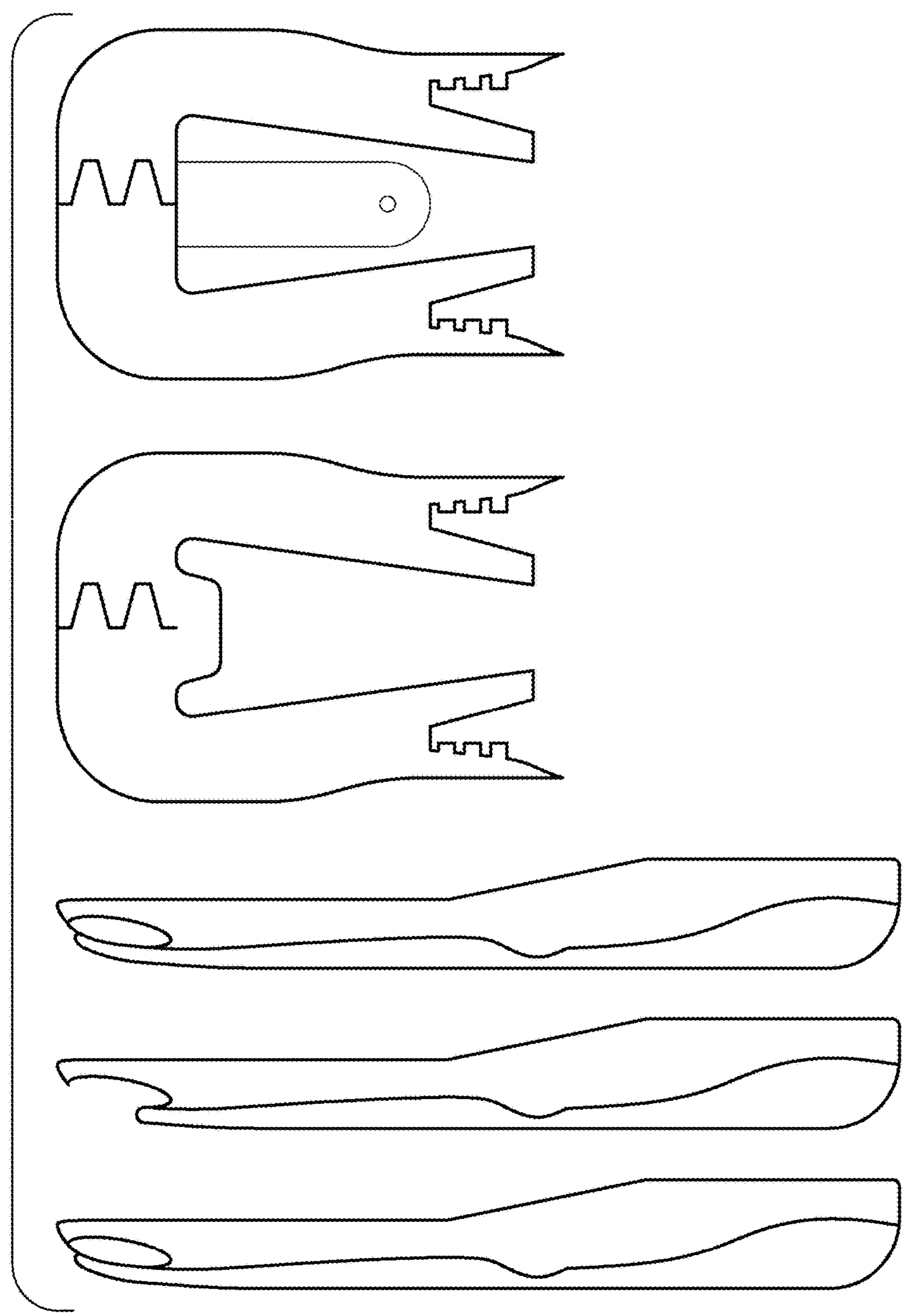

FIG. 15 illustrates a method of adjusting a length of a walking apparatus according to one aspect of the present disclosure. For example, a first user can be enabled to adjust a one or more characteristics of the walking apparatus such as a length and/or width to conform to a foot size a second user. The first user can include a doctor, a physician's assistant, a nurse, or a home healthcare working, just to name a few. The second user may a patient who does not have access rights to the mechanism that enables widening and/or lengthening of the walking apparatus. The first user can be enabled to adjust the length and/or length of the walking apparatus by being provided with an actuation tool such as a key, a wrench or a screwdriver that provides access to an actuation mechanism inside of the walking apparatus that varies its length and or width. The second user in one aspect of the present disclosure is not access to the actuation tool and thus is not enabled to adjust the length and/or width of the walking apparatus. When the length and or width of the walking apparatus is adjusted, in one aspect of the present disclosure, a predetermined radius of curvature of the outer sole of the walking apparatus can be maintained.

FIGS. 16A-16F illustrate various configurations of an outer sole of an adjustable walking apparatus according to certain aspects of the disclosure. The configurations depicted in FIGS. 16A-16F can be configured for any of the adjustable walking apparatuses described above, and can include an outer sole made up of a plurality of individual sections that are operatively coupled to one another, or a stretchable unitary structure that conforms to plurality of different lengths and widths.

It is understood, that any of the aspects illustrated, depicted, or described in the present disclosure, including in the figures, can be combined and/or used with any other aspect illustrated, depicted, or described in the present disclosure, including the figures. For example, each of the aspects set forth in the figures and/or described in the disclosure can be used in or combined with an open-toe orthopedic walking boot, a closed-toe orthopedic walking boot, an orthopedic walking boot including bilateral struts, an orthopedic walking boot including a clamshell configuration, a soft component of an orthopedic walking boot, a post-operative shoe (e.g., a shoe with a stiff base that can be worn on either the left foot or the right foot that can enable a patient to walk without reinjuring the toe(s) and/or foot), a clinical walker, and a hospital walker, just to name a few. Furthermore, it is understood that the length and/or width of a walking apparatus provided by the present disclosure can be adjusted to a plurality of positions to accommodate a plurality of foot sizes without departing from the spirit of the present disclosure. The scope of the present disclosure further includes that the length and/or the width of a walking apparatus provided by the present disclosure can be adjusted at the forefoot component, the midfoot component, and/or the heel component either independently or in an interconnected manner without departing from the spirit of the present disclosure.

The claims are not intended to be limited to the various aspects of this disclosure, but are to be accorded the full scope consistent with the language of the claims. It is noted that specific illustrative embodiments of the disclosure have been shown in the drawings and described in detail hereinabove. It is to be understood that various changes and modifications may be made without departing from the spirit and scope of the disclosure. All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "step for."

What is claimed is:

1. A walking apparatus, comprising: a sole having an adjustable length, the sole comprising: a heel portion; a forefoot portion operatively coupled to the heel portion, the forefoot portion configured for adjustment from a first position to at least one other position relative to the heel portion; wherein a length of the sole is configured to adjust from a first length to a second length when the forefoot portion is adjusted from the first position to the at least one other position, further comprising: at least one dorsal forefoot section having an adjustable width; and at least one side portion configured to enable an adjustment in the width of the at least one dorsal forefoot section when the forefoot portion is adjusted from the first position to the at least one other position.

2. The apparatus of claim 1, further comprising an actuator mechanism operatively coupled to at least one of the forefoot portion and the heel portion, the actuator mechanism configured to enable the adjustment of the forefoot portion from the first position to the at least one other position.

3. The apparatus of claim 2, wherein the actuator mechanism comprises: a cantilever configured for actuation; a plurality of arms operatively coupled to the cantilever; and a plurality of ridges; wherein the plurality of arms are configured for retention between the plurality of ridges.

4. The apparatus of claim 3, wherein when the cantilever is actuated, the plurality of arms are configured to clear a height of the plurality of ridges enabling the adjustment of the forefoot portion from the first position to the at least one other position.

5. The apparatus of claim 4, wherein the cantilever is spring loaded such that when the cantilever is no longer actuated, the plurality of arms are configured to return to the plurality of gaps between the plurality of ridges.

6. The apparatus of claim 4, wherein the forefoot portion comprises a surface configured to enable actuation of the cantilever.

7. The apparatus of claim 2, wherein the actuator mechanism comprises: an actuator; a spring operatively coupled to the actuator; an arm operatively coupled to the actuator, the arm including a plurality of ridges with a plurality of gaps therebetween; and a boss configured for retention in the plurality of gaps between the plurality of ridges.

8. The apparatus of claim 7, wherein when a force is applied to the actuator, the spring is configured to enable the boss to clear a height of the plurality of ridges enabling the adjustment of the forefoot portion from the first position to the at least one other position.

9. The apparatus of claim 8, wherein when the force is applied to the actuator the forefoot portion automatically adjusts from the first position to the at least one other position.

10. The apparatus of claim 7, further comprising a plurality of actuator mechanisms, wherein at least one actuator mechanism is positioned on opposing sides of the at least one of the forefoot portion and the heel portion.

11. The apparatus of claim 1, wherein the forefoot portion comprises an adjustable width.

12. The apparatus of claim 11, wherein the forefoot portion further includes an actuator configured to enable an adjustment in the width of the walking apparatus.

13. The apparatus of claim 12, wherein the actuator includes a cam that when rotated is configured widen and narrow the walking apparatus.

14. The apparatus of claim 13, wherein the cam includes an aperture configured to receive a tool that enables rotation.

15. The apparatus of claim 1, wherein the at least one side portion is formed with a tapered shape and is configured to remain stationary when the forefoot portion is adjusted from the first position to the at least one other position.

16. The apparatus of claim 15, wherein the tapered shape of the at least one side portion is configured to enable an expansion or a compression of the at least one dorsal forefoot section, when the forefoot portion is adjusted from the first position to the at least one other position.

17. A walking apparatus, comprising: a sole having an adjustable length, the sole comprising: a treaded surface; a heel portion; and a forefoot portion operatively coupled to the heel portion, the forefoot portion configured for adjustment from a first position to at least one other position relative to the heel portion; wherein a length of the sole is configured to adjust from a first length to a second length when the forefoot portion is adjusted from the first position to the at least one other position, and wherein when the length of the sole adjusts from the first length to the second length, a length of the treaded surface adjusts to traverse the second length of the sole.

18. A walking apparatus, comprising: a sole having an adjustable length, the sole comprising: a heel portion; and a forefoot portion operatively coupled to the heel portion, the forefoot portion configured for adjustment from a first position to at least one other position relative to the heel portion, wherein the heel portion and the forefoot portion form a radius of curvature of the sole, wherein a length of the sole is configured to adjust from a first length to a second length when the forefoot portion is adjusted from the first position to the at least one other position, and wherein the radius of curvature of the sole is maintained when the length of the sole adjusts from the first length to the second length.

* * * * *